(12) United States Patent
Chu et al.

(10) Patent No.: US 8,993,686 B2
(45) Date of Patent: Mar. 31, 2015

(54) MULTIAMINO ACID-BASED POLY(ESTER AMIDE)S

(75) Inventors: Chih-Chang Chu, Ithaca, NY (US); Mingxiao Deng, Jilin (CN)

(73) Assignee: Cornell University, Ithaca, NY (US)

( * ) Notice: Subject to any disclaimer, the term of this patent is extended or adjusted under 35 U.S.C. 154(b) by 239 days.

(21) Appl. No.: 13/262,418

(22) PCT Filed: Mar. 31, 2010

(86) PCT No.: PCT/US2010/000954
§ 371 (c)(1),
(2), (4) Date: Dec. 8, 2011

(87) PCT Pub. No.: WO2010/114601
PCT Pub. Date: Oct. 7, 2010

(65) Prior Publication Data
US 2012/0123064 A1    May 17, 2012

Related U.S. Application Data

(60) Provisional application No. 61/202,774, filed on Apr. 2, 2009, provisional application No. 61/177,516, filed on May 12, 2009, provisional application No. 61/272,936, filed on Nov. 20, 2009.

(51) Int. Cl.
| | | |
|---|---|---|
| C08G 69/08 | (2006.01) | |
| C08G 69/10 | (2006.01) | |
| C08G 69/44 | (2006.01) | |
| A61L 15/60 | (2006.01) | |
| A61L 15/26 | (2006.01) | |
| A61L 15/44 | (2006.01) | |
| A61L 26/00 | (2006.01) | |
| A61L 27/18 | (2006.01) | |
| A61L 27/54 | (2006.01) | |

(52) U.S. Cl.
CPC ............... *A61L 15/60* (2013.01); *A61L 15/26* (2013.01); *A61L 15/44* (2013.01); *A61L 26/0019* (2013.01); *A61L 26/0066* (2013.01); *A61L 26/008* (2013.01); *A61L 27/18* (2013.01); *A61L 27/54* (2013.01); *C08G 69/44* (2013.01); *A61L 2300/604* (2013.01)
USPC ........... 525/434; 525/420; 525/425; 525/432; 528/272; 528/288; 528/302; 528/310; 528/323; 528/325; 528/328

(58) Field of Classification Search
USPC .......... 525/420, 425, 432, 434; 528/272, 288, 528/302, 310, 323, 325, 328
See application file for complete search history.

(56) References Cited

U.S. PATENT DOCUMENTS

| | | |
|---|---|---|
| 5,455,027 A | 10/1995 | Zalipsky et al. |
| 2007/0167605 A1 | 7/2007 | Chu et al. |
| 2008/0171836 A1 | 7/2008 | Lee |
| 2008/0314289 A1 | 12/2008 | Pham et al. |

FOREIGN PATENT DOCUMENTS

| | | |
|---|---|---|
| WO | 02/18477 A2 | 3/2002 |
| WO | 2007/035938 A2 | 3/2007 |

OTHER PUBLICATIONS

Deng, M., et al., Synthesis and Characterization of Biodegradable Poly(ester amide)s with Pendant Amine Functional Groups and in Vitro Cellular Response, Biomacromolcules, Oct. 7, 2009, vol. 10, No. 11, pp. 3037-3047.
De Wit, M., et al., Syntheses, characterization, and functionalization of poly(ester amide)s with pendant amine functional groups, Journal of Polymer Science: Part A: Polymer Chemistry, Aug. 26, 2008, vol. 46, No. 19, pp. 6376-6392.

*Primary Examiner* — Ana Woodward
(74) *Attorney, Agent, or Firm* — Hodgson Russ LLP

(57) ABSTRACT

Biodegradable saturated and unsaturated polyester amides (PEA)s made from multiamino acid monomers and methods of making biodegradable saturated and unsaturated PEAs.

11 Claims, 16 Drawing Sheets a. PEA-Z-Lys-0

MULTIAMINO ACID-BASED POLY(ESTER AMIDE)S

FIELD

The present invention relates to biodegradable saturated and unsaturated polyester amides (PEA)s made from multiamino acid monomers and methods of making biodegradable saturated and unsaturated PEAs.

BACKGROUND

Amino acid-based biodegradable PEAs have been studied for many years due to their biocompatibility, biodegradability and mechanical properties. The presence of amide and ester bonds in PEA furnishes the PEA with a combination of properties typically exhibited by either polyesters or polyamides. Biodegradable PEA is typically synthesized with a solution polycondensation reaction of α-amino acids, aliphatic dicarboxylic acids (or dichloride of dicarboxylic acids) and diols (see Guo et al., Synthesis, Characterization, and Biodegradation of Copolymers of Unsaturated and Saturated Poly(ester amide)s. *Journal of Polymer Science, Part A: Polymer Chemistry* 2007; 45(9): 1595-1606).

PEA homopolymers generally do not have any functional groups located either along the PEA backbone chain or as pendant groups. However, the presence of functional pendant groups along the PEA backbone or as pendant groups could significantly expand the utility of PEA.

For example, functional groups would allow further chemical conjugations with a wide variety of drugs, biologically agents and/or active agents, thereby providing a novel route toward functionalized biomaterials. Built-in functional groups in PEAs could also provide an efficient method for tailoring the properties of PEA, such as hydrophilicity, degradation rate and mechanical strength.

The first reported synthesis of functional PEAs was based on a copolymer approach. A free functional group in the form of a carboxylic acid group was introduced in the lysine segment of the PEA copolymer. (see Jokhadze et al., Synthesis and Characterization of Functional Elastomeric Poly(ester Amide Co-polymers. *Journal of Biomaterials Science—Polymer Edition* 2007; 18(4):411-438)

In an alternative approach, carbon-to-carbon double bonds have been positioned along the backbone of PEA to provide a reactive site for the introduction of a functional group into PEA via unsaturated diacids or/and diols. The availability of these carbon-to-carbon double bonds in turn permits the fabrication of hydrogels by photo-gelation of PEA precursors, whereas PEA based upon saturated diacids or/and diols cannot be used to form hydrogels (see Guo et al., Synthesis, Characterization, and Biodegradation of Copolymers of Unsaturated and Saturated Poly(ester amide)s. *Journal of Polymer Science, Part A: Polymer Chemistry* 2007; 45(9): 1595-1606).

The present invention relates to an efficient and cost effective way to produce saturated and unsaturated PEAs with free pendant functional groups.

SUMMARY

The present invention relates to the synthesis and characterization of biodegradable PEAs having free pendant functional groups.

A first embodiment is a PEA of formula I:

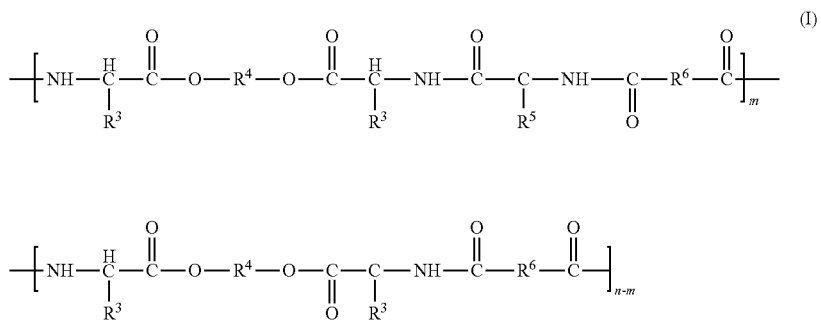

wherein m is about 0.1-0.9;

n is about 0.9 to 0.1;
$R^3$ is a residue of a first amino acid;
$R^4$ and $R^6$ are ($C_2$-$C_{20}$) alkylene; and
$R^5$ is a residue of a second amino acid having a pendant functional group selected from the group consisting of $NH_2$, COOH, and OH, and
wherein the pendant group is optionally protected, and wherein the PEA has a Mn of 1 to 500 kg/mol.

A second embodiment is a method for producing the PEA of the first embodiment by reacting a salt of an amino acid diester monomer with an amino acid N-carboxyanhydride monomer to obtain a reaction product (i.e., a derivative monomer), and reacting the derivative monomer with a nitrophenol diacid monomer to obtain the compound of formula I.

A third embodiment is a saturated polymer of formula (X):

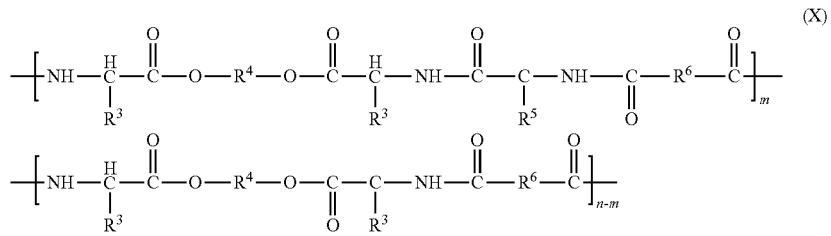

wherein m is about 0.1-0.9;
n is about 0.9 to 0.1;
$R^3$ is a residue of a first amino acid having a substituent group that does not need protection during peptide synthesis;
$R^4$ and $R^6$ are selected from the group consisting of ($C_2$-$C_{28}$) alkyloxy; ($C_2$-$C_{28}$) alkylene; ($C_2$-$C_{28}$) alkyloxy substituted with a side chain selected from the group consisting of (2-carboxyethyl)thio, (2-hydroxethyl)thio, (2-aminoethyl)thio and (2-aminoethyl)thio hydrochloride salt; or ($C_2$-$C_{28}$) alkylene substituted with a side chain selected from the group consisting of (2-carboxyethyl)thio, (2-hydroxethyl)thio, (2-aminoethyl)thio and (2-aminoethyl)thio hydrochloride salt; and
$R^5$ is a residue of a second amino acid has a pendant group selected from the group consisting of $NH_2$, COOH, and OH,
wherein the pendant group is optionally protected, and
wherein the PEA has a Mn of 1 to 500 kg/mol.

A fourth embodiment is directed to a method of making a polymer of formula (X).

A fifth embodiment is a composition comprising the PEAs disclosed in or produced by the first four embodiments. For example, in one aspect of this embodiment, the composition can be a gel.

The term "halo" herein means chloro, fluoro, bromo, or iodo.

Alkyl, alkenyl, alkynyl, etc. denote both straight and branched groups.

As used herein, "alkyl" means both branched and straight-chain saturated aliphatic hydrocarbon groups having a specified number of carbon atoms. Examples of alkyl include, but are not limited to, methyl, ethyl, n-propyl, i-propyl, n-butyl, s-butyl, t-butyl, n-pentyl, and s-pentyl.

"Alkylene" means herein both branched and straight-chain saturated aliphatic hydrocarbon groups having two open valences and having a specified number of carbon atoms. Examples of alkylene include, but are not limited to, methylene, ethylene, n-propylene, n-butylene, s-butylene, and n-pentylene.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy.

"Alkenyl" means herein hydrocarbon chains of either a straight or branched configuration having one or more unsaturated carbon-carbon bonds, which may occur in any stable point along the chain, such as ethenyl and propenyl.

"Alkynyl" means herein hydrocarbon chains of either a straight or branched configuration having one or more triple carbon-carbon bonds, which may occur in any stable point along the chain, such as ethynyl and propynyl.

"Aryl" denotes a phenyl radical or an ortho-fused bicyclic carbocyclic radical having about nine to ten ring atoms in which at least one ring is aromatic. Examples of aryl include, but are not limited to phenyl and naphthyl.

The term herein "amino acid" mean herein a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acid (e.g. phosphoserine; phosphotireonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; and tert-butylglycine) residue having one or more open valences.

The term "amino acid" also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a ($C_1$-$C_6$) alkyl phenyl or benzyl ester or amide). Other suitable amino and carboxy protecting groups are known to those skilled in the art (See for example, see Wuts et al., *Greene's. Protective Groups in Organic Synthesis,* 4th Edition, 2006; L. Stryer, Biochemistry, (3rd Ed), W.H. Freeman and Co.: New York, 1975; J. March, *Advanced Organic Chemistry, Reactions, Mechanisms and Structure,* (2nd Ed.), McGraw Hill: New York, 1977; F. Carey and R. Sundberg, *Advanced Organic Chemistry, Part B*; Reactions and Synthesis, (2nd Ed.), Plenum: New York, 1977; and references cited therein).

The term "amino acid" also includes alpha amino acids and beta amino acids. Alpha amino acids include monocarboxylic monoamino acids, dicarboxylic monoamino acids, polyamino acids and heterocyclic amino acids. Examples of monocarboxylic monoamino acids include glycine, alpha-phenylglycine, alpha-alanine, serine, valine, norvaline, beta-merceptovaline, threonine, cysteine, leucine, isoleucine, norleucine, N-methylleucine, beta-hydroxy leucine, methionine, phenylalanine, N-methylphenylalanine, pipecolic acid, sarcosine, selenocysteine, tyrosine, 3,5-diiodotyrosine, triiodothyronine, and thyroxine.

Examples of monoamino dicarboxylic acids and amides include aspartic acid, beta-methyl aspartic acid, glutamic acid, asparagine, alpha-aminoadipic acid, 4-keto-pipecolic acid, lanthionine, and glutamine. Examples of polyamino acids include ornithine, lysine, 6-N-methyllysine, 5-hydroxylysine, desmosine, argmine and cystine. Examples of heterocyclic amino acids include proline, 4-hydroxyproline and histidine, and tryptophan. Examples of other alpha amino acids are gamma-carboxyglutamate and citrulline. The beta amino acids include, for example, beta-alanine.

The term "biodegradable" is used herein to mean capable of being broken down by various enzymes such as trypsins, lipases and lysosomes in the normal functioning of the human body, living organisms (e.g., bacteria) and/or water environment.

The term "biomaterial" is used herein to mean a synthetic material used to function in intimate contact with living tissue.

The term "bioactive agent" is used herein to mean agent for delivery to cells, tissues or organs for nutrient or therapeutic effects. These include, but are not limited to nutrients, pharmaceuticals, drugs, peptides and oligo nucleotides.

The term "hydrogel" is used herein to mean a polymeric material which exhibits the ability to swell in water and to retain a significant portion of water within its structure without dissolution.

The term "biodegradable hydrogel" is used herein to mean hydrogel formed by cross-linking a polymer which is degraded by water and/or by enzymes found in nature.

The term "hydrogel precursor" is used herein to mean water soluble polymer that is photocrosslinkable in solution in a medium to form a hydrogel The term "photocrosslinking" is used herein to mean causing vinyl bonds to break and form cross-links by the application of radiant energy.

The term "Gel permeation chromatography ("GPC")" refers to the separation method for the determination of molecular weight averages (Mn) and molecular weight distributions (PDI=Mw/Mn) of polymers.

The term "PEA-COOH" means herein a PEA with free carboxylic groups.

The term "PEA-NH$_2$" means herein a PEA with free amine groups. The term "PEA-AANCA-#" means herein a PEA with protected amino acids. The "#" indicates the ratio/amount of the protected amino acid present in the PEA.

The term "De-PEA-AANCA-#" means herein a PEA with amino acid units after deprotection to restore pendant functional groups. The "#" indicates the ratio/amount of amino acid present in the PEA. For example, the term "De-PEA-LysNCA-25" means a PEA with a lysine that provides a pendant functional group (after deprotection), wherein m is 75 and n is 25 (see compound of formula I).

The term "TosOH" means herein p-toluenesulfonic acid monohydrate.

The term "NEt3" means herein triethylamine.

The term "EtAc" means herein Ethyl acetate.

The term "TFA" means herein trifluoroacetic acid.

The term "DMA" means herein N,N-Dimethylacetamide.

DETAILED DESCRIPTION OF THE INVENTION

Figure 1A:
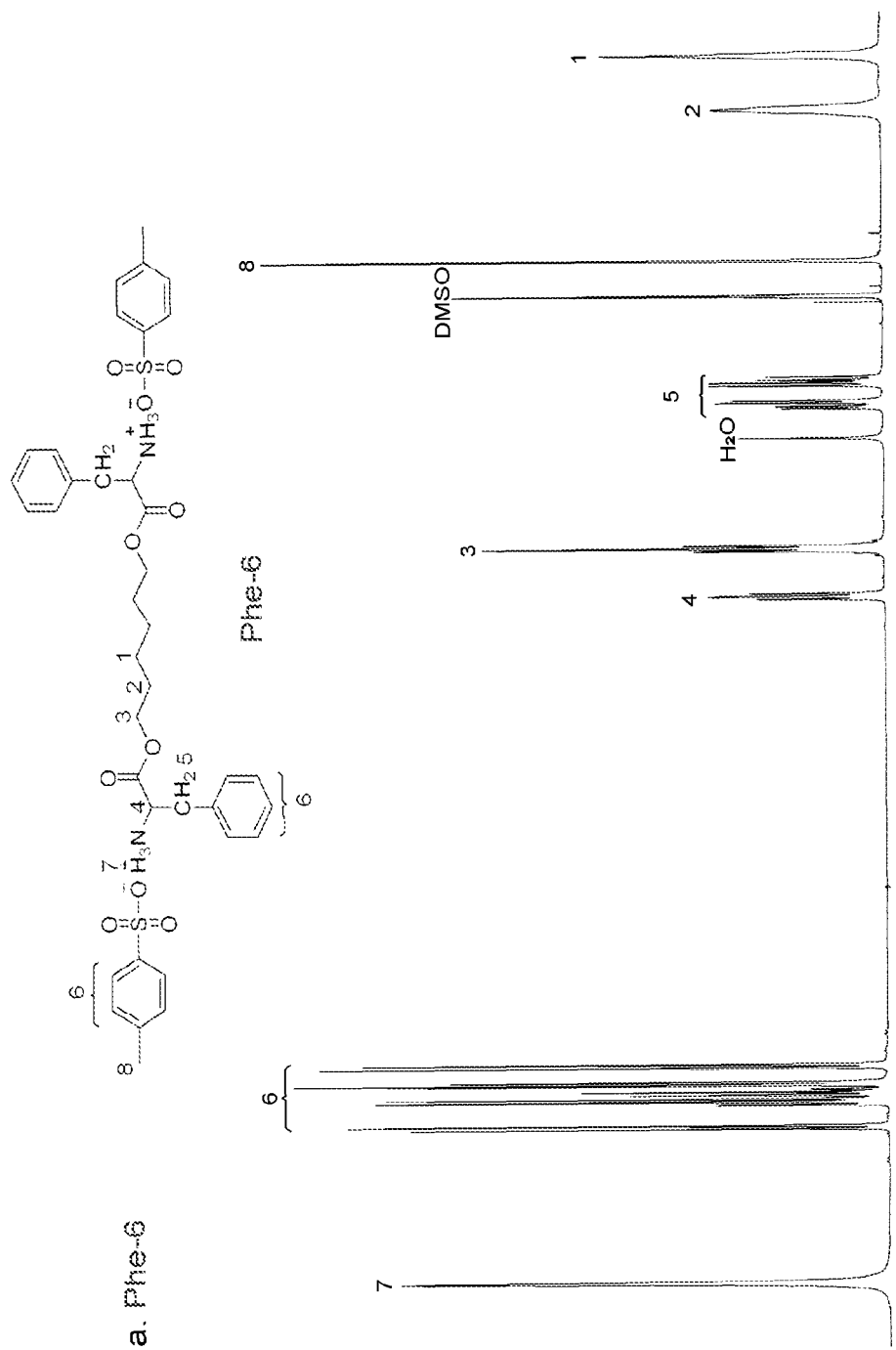
FIG. 1 displays an $^1$H NMR spectra of two monomers (a) Phe-6 and (b) Z-Lys-Phe-6.

The present invention relates to the synthesis and characterization of biodegradable PEAs having free pendant functional groups. The PEAs are made from multiamino acid monomers and have at least one functionality, such as —NH$_2$, —OH, and —COOH, located within the same monomer or block as another amino acid.

In a first embodiment, the PEA has a formula as follows:

$$\left[ NH-\underset{R^3}{\underset{|}{\overset{H}{C}}}-\overset{O}{\overset{\|}{C}}-O-R^4-O-\overset{O}{\overset{\|}{C}}-\underset{R^3}{\underset{|}{\overset{H}{C}}}-NH-\overset{O}{\overset{\|}{C}}-\underset{R^5}{\underset{|}{C}}-NH-\underset{O}{\underset{\|}{C}}-R^6-\overset{O}{\overset{\|}{C}} \right]_m \quad (I)$$

$$\left[ NH-\underset{R^3}{\underset{|}{\overset{H}{C}}}-\overset{O}{\overset{\|}{C}}-O-R^4-O-\underset{O}{\underset{\|}{C}}-\underset{R^3}{\underset{|}{C}}-NH-\overset{O}{\overset{\|}{C}}-R^6-\overset{O}{\overset{\|}{C}} \right]_{n-m}$$

wherein m is about 0.0-1.0, preferably 0.1-0.9, and more preferably 0.25-0.75;

wherein n is about 1.0-0.0, preferably 0.9 to 0.1, and more preferably 0.25-0.75;

R$^3$ is a residue of a first amino acid;

R$^4$ and R$^6$ are (C$_2$-C$_{20}$) alkylene; and

R$^5$ is a residue of a second amino acid having a pendant group selected from the group consisting of NH$_2$, COOH, and OH, and wherein the pendant group is optionally protected, and wherein the PEA has a Mn of 1 to 500 kg/mol.

In one aspect of the invention, a homopolymer of the PEA is formed when n=m. A random copolymer of a multiamino acid PEA is formed when 0<m<n.

As to R$^3$, the residue of a first amino acid is the portion of an amino acid that is present in the PEA once the PEA has been synthesized. In one aspect of this embodiment, the first amino acid is any amino acid that has one free NH$_2$ group and one free COOH group. In yet another aspect of this embodiment, the first amino acid is an amino acid that does not require a protective group during the synthesis of PEA.

In one aspect of the invention, the residue is the side chain of the amino acid and the α-carbon, amino group and carboxylic acid of the amino acid is removed.

In yet another aspect, the first amino acid is selected from the group consisting of Phe, Arg, Val, Leu, Ile, Nle, Gly, Ala, or Met. The residue is preferably selected from the group consisting of

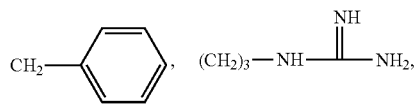

$CH(CH_3)_2$, $CH_2CH(CH_3)_2$, $CH(CH_3)CH_2CH_3$, $(CH_2)_3CH_3$, H, $CH_3$, and $(CH_2)_2SCH_3$, respectively.

As to $R^5$, the residue of a second amino acid is the portion of the second amino acid that is present in the PEA once the PEA has been synthesized. The second amino acid can be an amino acid that is either the same or different from the first amino acid.

In one facet of this embodiment, the second amino acid is preferably an amino acid selected from the group consisting of Thr, Tyr, Pro, Trp, Cys, Lys, Ser, Asp, and Glu. The second amino acid is preferably an amino acid that provides PEA with a free pendant functional group selected from the group consisting of $NH_2$, OH, and COOH. For example, the second amino acid can be Lys, Ser, Asp, and Glu.

In one aspect of the invention, the residue is the side chain of the amino acid and the α-carbon, amino group and carboxylic acid of the amino acid is removed. The residue of the second amino acid is preferably $(CH_2)_4NH_2$, $CH_2OH$, $CH_2COOH$, and $(CH_2)_2COOH$, respectively. Lys provides a free $NH_2$ pendant group. Ser provides a free OH pendant group. Asp and Glu provide a free COOH pendant group.

The free pendant functional group of the second amino acid is optionally protected with a protective group selected from the group consisting of methyl, formyl, ethyl, acetyl, t-butyl, anisyl, benzyl, trifluoroacetyl, N-hydroxysuccinimide, t-Butyloxycarbonyl, benzoyl, 4-methylbenzyl, thioanizyl, thiocresyl, benzyloxymethyl, 4-nitrophenyl, benzyloxycarbonyl, 2-nitrobenzoyl, 2-nitrophenylsulphenyl, 4-toluenesulphonyl, pentafluorophenyl, diphenylmethyl (Dpm), 2-chlorobenzyloxycarbonyl, 2,4,5-trichlorophenyl, 2-bromobenzyloxycarbonyl, 9-fluorenylmethyloxycarbonyl, tripheylmethyl, and 2,2,5,7,8-pentamethyl-chroman-6-sulphonyl (see Wuts et al., *Greene's Protective Groups in Organic Synthesis*, 4th Edition, 2006, the entirety of which is hereby incorporated by reference). In one facet of this embodiment, the protective group is a benzyloxycarbonyl (Z) protective group.

The protective groups of the resulting PEAs are completely removed to produce PEAs having free pendant functional groups selected from the group consisting of $NH_2$, COOH, and OH.

In yet another aspect of this embodiment, the PEA contains residues from at least three different amino acids. The residue of a third amino acid is the portion of the third amino acid that is present in the PEA once the PEA has been synthesized. The third amino acid is preferably an amino acid that has at least one free $NH_2$ group and one free COOH group. Examples of residues of a third amino acid include Ala, Arg, Asn, Asp, Cys, Glu, Gln, Gly, His, Hyl, Hyp, Ile, Leu, Lys, Met, Phe, Pro, Ser, Thr, Trp, Tyr, and Val.

In one aspect of the invention, the residue is the side chain of the amino acid and the α-carbon, amino group and carboxylic acid of the amino acid is removed. In another aspect, the residue of the third amino acid is optionally selected from the group consisting of $(CH_2)_4NH_2$, $CH_2OH$, $CH_2COOH$, $(CH_2)_2COOH$,

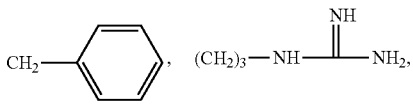

$CH(CH_3)_2$, $CH_2CH(CH_3)_2$, $CH(CH_3)CH_2CH_3$, $(CH_2)_3CH_3$, H, $CH_3$, and $(CH_2)_2SCH_3$, respectively. The third amino acid may or may not provide the PEA with a free pendant group selected from the group consisting of COOH, OH, and $NH_2$.

The third amino acid is present in the PEA in the form of a second m or n monomer. For example, PEA having at least three amino acids contains $m_1$, $m_2$ and $n_1$ monomers, wherein the $m_1$ and $m_2$ monomers each have a different residue of an amino acid. Alternatively, the PEA is composed of $m_1$, $n_1$ and $n_2$ monomers, wherein the $n_1$ and $n_2$ monomers each have a different residue of an amino acid. For example, a PEA is produced that contains $m_1$, wherein $R^3$ of $m_1$ is

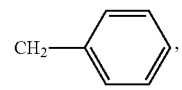

$R^5$ of $m_1$ is $(CH_2)_4NH_2$, and $R^3$ of $m_2$ is

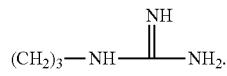

A biodegradable PEA with free pendant groups along the polymer backbone is produced. The PEA has at least two residues of an amino acid, which are separated by a peptide bond, in a single unit. In other words, the PEA has two amino acids that are adjacent without the need for a spacer or ester group. At least one of the residues of an amino acid provides a free pendant functional group. The presence of free pendant functional groups allows for the coupling of biologically or chemically active agents, such as drugs and other compounds.

In yet another aspect of this embodiment, the end groups of the monomers will vary. For example, when electrophilic monomers are in excess, the end groups are p-nitrophenyl groups (the derivative of carboxylic group) as illustrated:

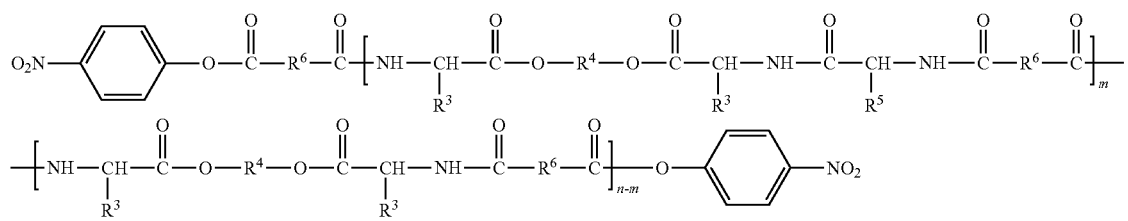

Formula I-A

When the nucleophilic monomers are in excess, the end groups are amine groups as illustrated:

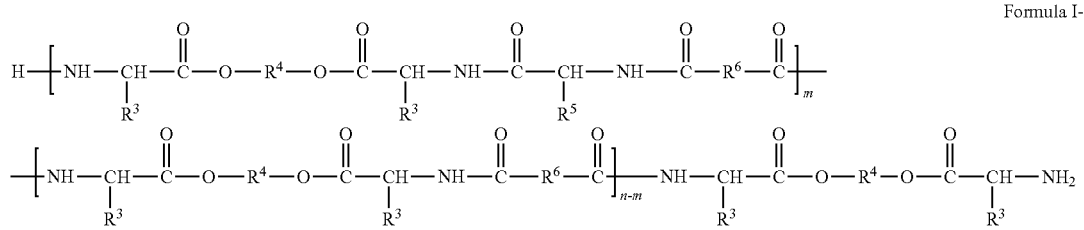

Formula I-B

When the monomers have an equal molar ratio, one end group is p-nitropheny group, and another end group is an amine group as illustrated:

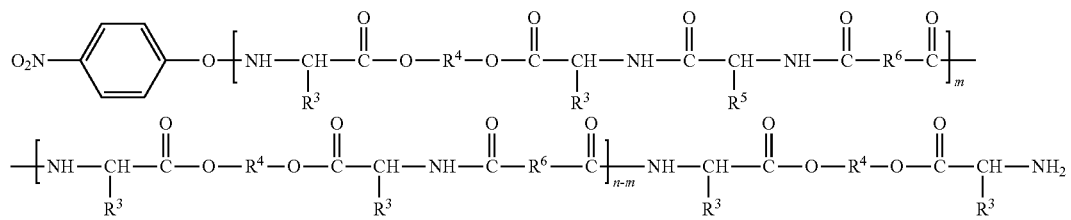

Formula I-C

We now turn to the second embodiment.

The PEA of the first embodiment is produced by reacting a salt of an amino acid diester monomer with an amino acid N-carboxyanhydride monomer to obtain a reaction product. The amino acid N-carboxyanhydride monomer is optionally provided with a protective group. The protective group is present throughout the method and carried over to the compound of formula I, if present. The reaction product is a derivative monomer containing an amino acid residue of the amino acid N-carboxyanhydride monomer and an amino acid residue of an amino acid diester monomer, along with the protective group, if present. This step can be carried out in accordance with Knobler et al. Reaction of N-carboxy-alpha-amino acid anhydrides with hydrochlorides of hydroxylamine, O-alkylhydroxylamines, and amines; syntheses of aminohydroxamic acids, amidooxy peptides, and alpha-amino acid amides. *Journal of the Chemical Society* 1964 (October):3941-3951; and Knobler et al., α-Aminoacyl derivatives of aminobenzoic acid and of aminooxy acids by reaction of their hydrochlorides with amino acid N-carboxyanhydrides. *Journal of the Chemical Society [Section] C: Organic* 1969(14):1821-1824.

In a subsequent step, the derivative monomer is then reacted with a diacid monomer to obtain the compound of formula I. In one facet of the embodiment, solution polycondensation of the reaction product with the diacid monomer is carried out to obtain the compound of formula I. A deprotection step is carried out to remove the protective groups, if present. The removal of the protective groups results in a free pendant functional groups on the PEA.

The PEA is optionally purified. The PEA is placed for example in a mixed solution of trifluoroacetic acid and methanesulfonic acid. The PEA is precipitated out of the mixed solution with a precipitating agent such as diethyl ether. The precipitated PEA is then dissolved in an organic solvent, such as DMF. The solvent is optionally neutralized with a solution such as triethylamine, followed by precipitation with an aqueous solution, such as water.

The amount of monomers to be incorporated into PEA would depend on the desired content of the amine groups on the final PEA polymer, which can be controlled via varying the molar ratio of added monomers. For example, in producing the PEA, the feed molar ratio of starting materials can be adjusted to vary the amount of m and n present in the PEA. In one feature, the amount of amino acid diester to amino acid N-carboxyanhydride monomer to diacid monomer is from 0.1-20.0:0.1-1.0:0.1-20.0 and preferably is 2.0:1.0:2.0.

The amino acid diester monomer is prepared by reacting an amino acid and diol in a solution containing an organic solvent (e.g., toluene) and acid (e.g. as p-toluenesulfonic acid monohydrate). An amino acid can be converted into a bis-α-amino acid) diester monomer, for example, by condensing the amino acid with a diol (e.g., OH—$(CH_2)_n$OH, wherein n is 1-8). As a result, ester bonds are formed.

The amino acid-based diester monomer in one feature of this embodiment is di-p-toluenesulfonic acids salt of a bis(α-amino acid)α, ω-alkylene diester. Di-p-toluene sulfonic acid salts of bis-amino acid esters can be prepared as described in U.S. Pat. No. 6,503,538. For example, the amino acid-based diester monomer can be a di-p-toluenesulfonic acid salt of a bis-(1-α-amino acid)-alpha, ω-alkylene diester as follows:

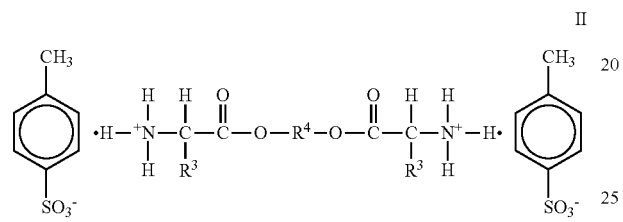
(II)

wherein $R^3$ is independently iso-butyl or benzyl; and $R^4$ is $(CH_2)_4$, $(CH_2)_6$, or $(CH_2)_{12}$.

In yet another example, a specific di-p-toluenesulfonic acid salts of L-lysine arylalkyl esters that can be used in accordance with this embodiment are:

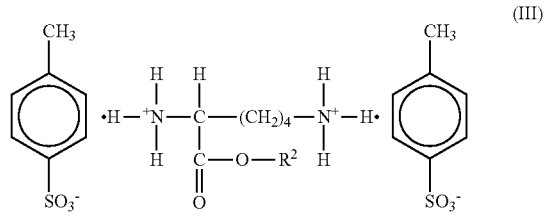
(III)

wherein $R^2$ is benzyl sec-phenethyl, or methylbenzyl. More specifically, $R^2$ can be benzyl.

The amino acid N-carboxyanhydride monomer is prepared by reacting an amino acid with a carbonyl chloride compound (e.g., triphosgene).

A feature of this embodiment is that the amino acid in the amino acid N-carboxyanhydride monomer is in accordance with the second amino acid of the first embodiment.

The amino acid N-carboxyanhyride optionally has a protective group. In one facet of this embodiment, the protective group is a benzyloxycarbonyl (Z) protective group.

The diacid monomers can be prepared in a number of ways including reacting a diacyl chloride (e.g., sebacoyl chloride) with a phenol (e.g., p-nitrophenol). The diacid monomers can also be prepared in accordance with U.S. Pat. No. 6,503,538.

For example, the diacid monomer can be a compound of formula IV:

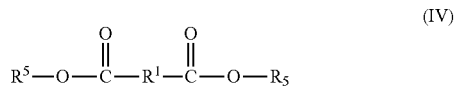
(IV)

wherein $R^1$ is $(CH_2)_4$, $(CH_2)_8$, or $(CH_2)_{12}$; and $R^5$ is p-nitrophenyl.

In another example, the compound is a compound of the formula V:

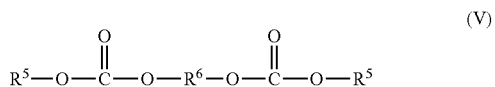
(V)

wherein $R^5$ is p-nitrophenyl; and $R^6$ is $(CH_2)_3$ or $(CH_2)_2$—O—$(CH_2)_2$.

A preferred feature of this embodiment is that the diacid monomer is selected from the group consisting of di-p-nitrophenyl adipate, di-p-nitrophenyl sebacinate, di-p-nitrophenyl sebacate and di-p-nitrophenyl dodecyldicarboxylate.

In yet another aspect of this embodiment, a PEA is produced that contains residues from at least three different amino acids. The PEA is produced in accordance with the first and second embodiments, but with the exception that the third amino acid is introduced into the PEA in the form of a second m or n monomer. For example, PEA having at least three amino acids may contain $m_1$, $m_2$ and $n_1$ monomers, wherein the $m_1$ and $m_2$ monomers each have a different residue of an amino acid.

Alternatively, the PEA is composed of $m_1$, $n_1$ and $n_2$ monomers, wherein the $n_1$ and $n_2$ monomers each have a different residue of an amino acid. For example, a PEA can be produced that contains a $m_1$, wherein $R^3$ of $m_1$ is

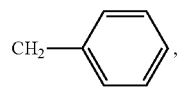, $R^5$ of $m_1$ is $(CH_2)_4NH_2$, and $R^3$ of $m_2$ is

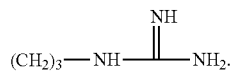.

The third embodiment is PEA of formula (X):

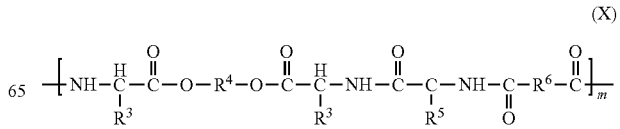
(X)

-continued

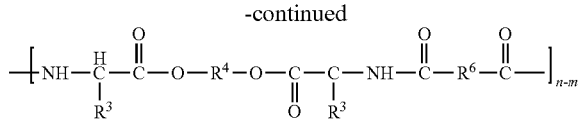

wherein m is about 0.1-0.9;
n is about 0.9 to 0.1;
$R^3$ is a residue of a first amino acid having a substituent group that does not need protection during peptide synthesis;
$R^4$ and $R^6$ are selected from the group consisting of ($C_2$-$C_{28}$) alkyloxy; ($C_2$-$C_{28}$) alkylene; ($C_2$-$C_{28}$) alkyloxy substituted with a side chain selected from the group consisting of (2-carboxyethyl)thio, (2-hydroxethyl)thio, (2-aminoethyl)thio and (2-aminoethyl)thio hydrochloride salt; or ($C_2$-$C_{28}$) alkylene substituted with a side chain selected from the group consisting of (2-carboxyethyl)thio, (2-hydroxethyl)thio, (2-aminoethyl)thio and (2-aminoethyl)thio hydrochloride salt; and
$R^5$ is a residue of a second amino acid has a pendant group selected from the group consisting of $NH_2$, COOH, and OH,
wherein the pendant group is optionally protected,
wherein the PEA has a Mn of 1 to 500 kg/mol.
In one aspect of this embodiment, $R_4$ and $R_6$ provides an unsaturated carbon to carbon bond The residues of the first and second amino acids are in accordance with those discussed for the first and second embodiments.

The end groups of the monomers are also in accordance with those discussed above.

We turn now to the fourth embodiment.

Unsaturated PEAs (UPEAs) are prepared by solution polycondensation of either (1) di-p-toluenesulfonic acid salts of bis(alpha-amino acid) diesters of unsaturated diol and di-p-nitrophenyl ester of saturated dicarboxylic acid or (2) di-p-toluenesulfonic acid salts of bis(alpha-amino acid) diesters of saturated diol and di-nitrophenyl ester of unsaturated dicarboxylic acid or (3) di-p-toluenesulfonic acid salt of bis(alpha-amino acid) diesters of unsaturated diol and di-nitrophenyl ester of unsaturated dicarboxylic acid.

Salts of p-toluenesulfonic acid are known for use in synthesizing polymers containing amino acid residues. The aryl sulfonic acid salts are used instead of the free base because the aryl sulfonic acid salts of bis(alpha-amino acid) diesters are easily purified through recrystallization and render the amino groups as unreactive ammonium tosylates throughout workup.

The di-p-nitrophenyl esters of unsaturated dicarboxylic acid can be synthesized from p-nitrophenol and unsaturated dicarboxylic acid chloride, e.g., by dissolving triethylamine and p-nitrophenol in acetone and adding unsaturated dicarboxylic acid chloride dropwise with stirring at −78° C. and pouring into water to precipitate product. Suitable acid chlorides are dicarboxylic acyl chlorides including, for example, fumaric, maleic, mesaconic, citraconic, glutaconic, itaconic, ethenyl-butane dioic and 2-propenyl-butanedioic acid chlorides.

The di-p-toluenesulfonic acid salts of bis(alpha-amino acid) diesters of unsaturated diol can be prepared by admixing amino acid, aryl sulfonic acid (e.g., p-toluenesulfonic acid monohydrate) and unsaturated diol in toluene, heating to reflux temperature, until water evolution is minimal, then cooling. The unsaturated diols include, for example, 2-butene-1,4-diol and 1,18-octadec-9-en-diol.

Di-p-nitrophenyl esters of saturated dicarboxylic acid and di-p-toluenesulfonic acid salts of bis(alpha-amino acid) diesters of saturated diol can be prepared as described in U.S. Pat. No. 6,503,538 B1.

This aspect of the embodiment is also supported by experiments and conclusions set forth in Guo, K., et al., *Journal of Polymer Science, Part A: Polymer Chemistry* 43(7), 1463-1477 (15 Feb. 2005), the whole of which is incorporated herein by reference.

UPEA is functionalized by reacting a thiol-based compound with the polymers. The thiol-based compounds contain a thiol group and a functional group. In one facet of this embodiment, the thiol-based compound is selected from the group consisting of 3-mercaptopropionic acid, cysteamine, 2-mercaptoethanol, sodium-3 mercapto 1-propane-sulfonate, and 2-aminoethanethiol hydrochloride. In yet another facet, the functional group is selected from the group consisting of $NH_2$, $NH_2HCl$, COOH, a sulfonic group and OH. The thiol group of the thiol-based compound attaches via a carbon to carbon double bond within the UPEA, resulting in a free pendant functional group along the backbone of the polymers, respectively.

UPEA is mixed with a thiol-based compound and an organic solvent such as DMA, DMSO, DMF, or combinations thereof to form a mixture. The mixture is heated to produce the desired polymer. The mixture is preferably heated at a temperature of 50° C. to 120° C., preferably 60° C. to 80° C., and more preferably 70° C. for a time of 12-36 hours, and preferably 24 hours.

In another aspect of this embodiment, an initiator is used in the reaction. For example, a thiol-ene reaction is a reaction, which can proceed in the presence of a radical initiator such as Azobisisobutyronitrile (AIBN), between a thiol moiety and an unconjugated C=C double bond to form a thioether. The UPEA (or UPEEA) polymers have double bonds along the polymer backbone available for radical addition of various thiols to provide a variety of different pendant functional groups, which could be used as the active covalent attaching sites for biologically active agents or drugs. For example, radical addition of thiols to the double bonds of a compound is carried out at 50-100° C. using AIBN as a radical initiator in DMF.

The reaction results in UPEA substituted with a side chain, such as (2 carboxyethyl)thio, (2-hydroxethyl)thio, (2-aminoethyl)thio, and (2-aminoethyl)thio hydrochloride salt produced based polymer is obtained.

A fifth embodiment of the invention is a composition containing the PEA of the first embodiment. A variety of compositions can be produced with the PEA of the first embodiment, including membranes, gels, hydrogels, blood coagulation products, wound healing products, bone regeneration materials, tissue engineering scaffolding, contact lenses, dental equipment, seed coatings, fertilizer, controlled agrochemical release compositions, dietary food additives, preservatives, antimicrobial textile finishes, wastewater treatment materials, cosmetics, lotions, moisturizers.

In order to form a composition, the functional group(s) on the PEA are substituted, directly or indirectly with a linker, with a bioactive and/or active material. When the PEA has pendant COOH or OH groups, the COOH and OH groups are substituted with a positively charged active material. When the PEA has a free pendent $NH_2$ group, the $NH_2$ groups are substituted with negatively charged active materials.

The bioactive and/or active material is selected from the group consisting of a peptide, antibiotic, drug, polypeptide, anti-inflammatory agent, anti-platelet agent, anti-coagulation agent, immuno-suppressive agents, nitric oxide derivative, antimicrobial agents, growth factors, polymers, fluorescent compounds (e.g., fluorescein), hydrogel forming polymers, gel forming polymers, and combinations thereof.

As used herein, a "peptide" is a sequence of 2 to 25 amino acids (e.g. as defined hereinabove) or peptidic residues having one or more open valences. The sequence may be linear or cyclic. For example, a cyclic peptide can be prepared or may result from the formation of disulfide bridges between two cysteine residues in a sequence. A peptide can be linked through the carboxy terminus, the amino terminus, or through any other convenient point of attachment, for example, through the sulfur of a cysteine. Peptide derivatives can be prepared as disclosed in U.S. Pat. Nos. 4,612,302; 4,853,371; and 4,684,620. Peptide sequences specifically recited herein are written with the amino terminus on the left and the carboxy terminus on the right. A preferred peptide is GRGD.

One or more of an antibiotic and/or drug can be directly or indirectly linked to the functional group of the PEA. Suitable antibiotics include β-lactam antibiotics (e.g., penicillin derivatives, cephalosporins, monobactams, carbapenems, and β-lactamase inhibitors), Adriamycin PFS/RDF® (Pharmacia & Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS Pharmacia & Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). Suitable antimetabolites include Cytostar-U® (Pharmacia & Upjohn), Fludara® (Berlex), Sterile FUDR® (Roche Laboratories), Leustatin® (Ortho Biotech), Methotrexate® (Immunex), Parinethol® (Glaxo Wellcome), Thioguanine® (Glaxo Wellcome) and Xeloda® (Roche Laboratories).

A drug is a therapeutic agent or a diagnostic agent and includes any substance, other than food, used in the prevention, diagnosis, alleviation, treatment, or cure of a disease. Stedman's Medical Dictionary 25 th Edition, Illustrated (1990) p. 486. The substance can be taken by mouth; injected into a muscle, the skin, a blood vessel, or a cavity of the body; or topically applied. Mosby's Medical, Nursing & Allied Health Dictionary, Fifth Edition, (1998) p. 516. The drug can include any substance disclosed in at least one of: The Merck Index, 12 th Edition (1996); Concise Dictionary of Biomedicine and Molecular Biology. Pei-Show Juo, (1996); U.S. Pharmacopeia Dictionary 2000 Edition; and Physician's Desk Reference, 2001 Edition. Specifically, the drug can include, but is not limited to, one or more: polypeptides, therapeutic antibodies abeiximab, anti-inflammatory agents, blood modifiers, anti-platelet agents, anti-coagulation agents, immune suppressive agents, anti-cell proliferation agents, and nitric oxide releasing agents. In one facet of this embodiment, the antibiotic and/or drug is a β-lactam compound such as a penicillin (e.g., penicillin V, penicillin G, procaine benzylpenicillin, or benzathine pencillin).

The attachment of a penicillin to PEA is exemplified as follows:

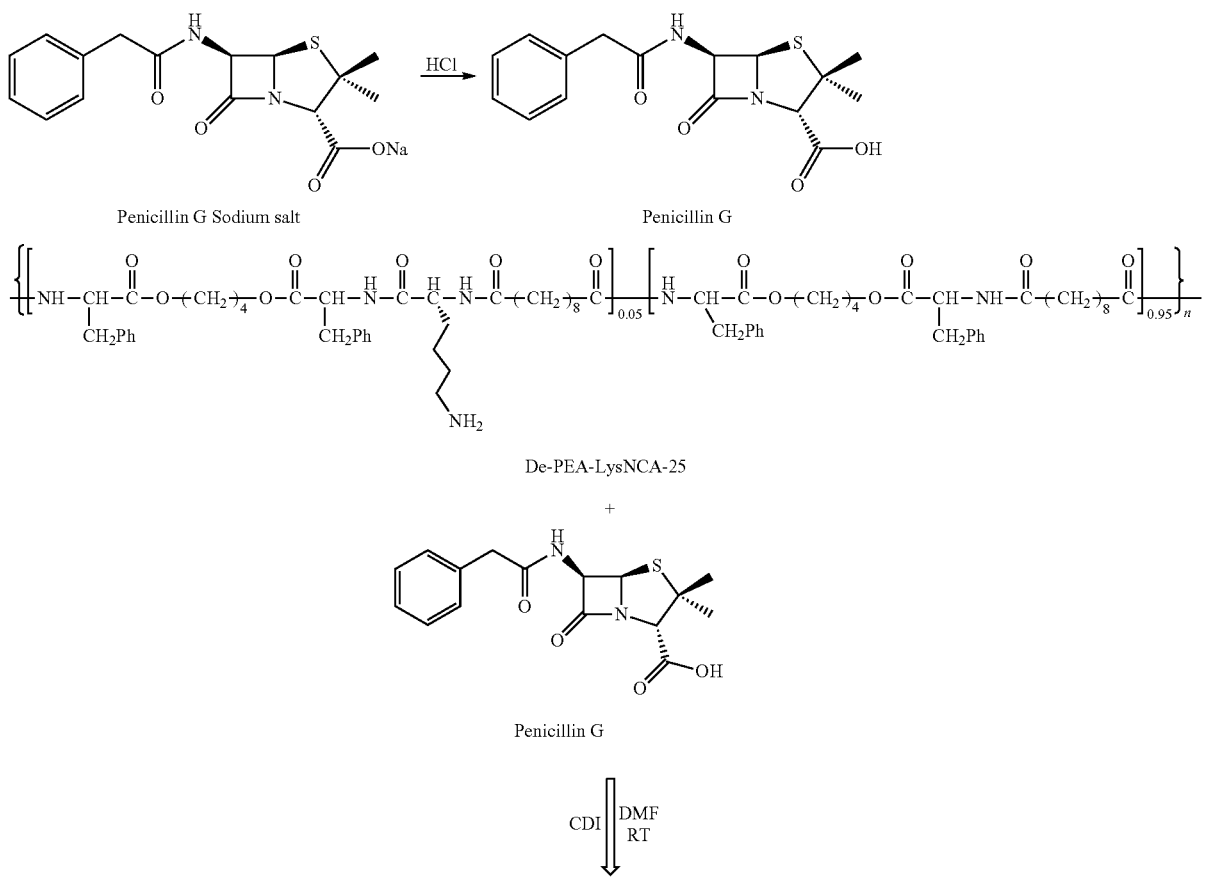

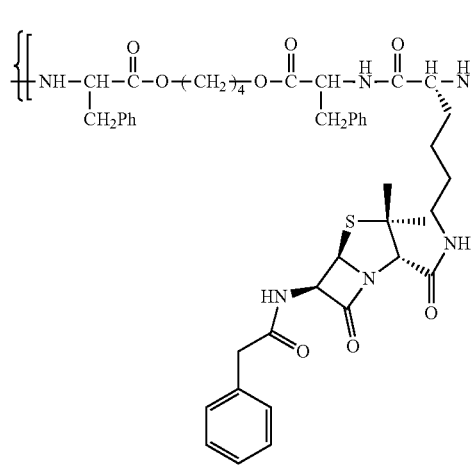

Polypeptides can have any suitable length. Specifically, the polypeptides can be about 2 to about 5,000 amino acids in length, inclusive; about 2 to about 2,000 amino acids in length, inclusive; about 2 to about 1,000 amino acids in length, inclusive; or about 2 to about 100 amino acids in length, inclusive.

The polypeptides can also include "Peptide mimetics". Peptide analogs are commonly used in the pharmaceutical industry as non-peptide drugs with properties analogous to those of the template peptide. These types of non-peptide compound are termed "peptide mimetics". Fauchere, J. (1986) *Adv. Drug Res.* 15:29; Veber and Freidinger (1985) *TINS* p. 392; and Evans et al. (1987) *J. Med. Chem.*, 30: 1229; and are usually developed with the aid of computerized molecular modeling.

Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH$_2$NH—, —CH$_2$S—, —CH$_2$—CH$_2$—, —CH=CH—(cis and trans), —COCH$_2$—, —CH(OH)CH$_2$—, and —CH$_2$SO—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A F., *Vega Data* (March 1983), Vol. 1, Issue 3, "Peptide Backbone Modifications" (general review); Morley, J. S., *Trends. Pharm. Sci.*, (1980) pp. 463-468 (general review); Hudson, D. et al., *Int J. Pept. Prot. Res.*, (1979) 14:177-185 (—CH$_2$NH—, —CH$_2$CH$_2$—); Spatola, A. F. et al., *Life Sci.* (1986) 38:1243-1249 (—CH$_2$—S—); Hann, M. M., *J. Chem. Soc. Perkin Trans I* (1982) 307-314 (—CHH—, cis and trans); Almquist, R. G. et al., *J. Med. Chem.*, (1980) 23:1392-1398 (—COCH$_2$—); Jennings-White, C. et al., *Tetrahedron Lett.*, (1982) 23:2533 (—COCH$_2$—) Szelke, M. et al., European Appln., EP 45665 (1982) CA: 97:39405 (1982) (—CH(OH) CH$_2$—); Holladay, M. W. et al., *Tetrahedron Lett.*, (1983) 24:4401-4404 (—CH(OH)CH$_2$—); and Hruby, V. J., *Life Sci.*, (1982) 31:189-199 (—CH$_2$—S—).

Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenic ity, and others.

Additionally, substitution of one or more amino acids within a polypeptide with a D-amino acid of the same type (e.g., D-lysine in place of L-lysine) can be used to generate more stable polypeptides and polypeptides resistant to endogenous proteases.

In one aspect, the polypeptide can be an antibody. Examples of such antibodies include single-chain antibodies, chimeric antibodies, monoclonal antibodies, polyclonal antibodies, antibody fragments, Fab fragments, IgA, IgG, IgM IgD, IgE and humanized antibodies. In one embodiment, the antibody can bind to a cell adhesion molecule, such as a cadherin, integrin or selectin. In another case, the antibody can bind to a molecule, such as collagen, elastin, fibronectin or laminin.

In yet another facet of this embodiment, the antibody can bind to a receptor, such as an adrenergic receptor, B-cell receptor, complement receptor, cholinergic receptor, estrogen receptor, insulin receptor, low-density lipoprotein receptor, growth factor receptor or T-cell receptor. Antibodies of the invention can also bind to platelet aggregation factors (e.g., fibrinogen), cell proliferation factors (e.g., growth factors and cytokines), and blood clotting factors (e.g., fibrinogen).

In another case, an antibody can be conjugated to an active agent, such as a toxin. For example, the antibody can be Abciximab (ReoPro®). Abeiximab is an Fab fragment of a chimeric antibody that binds to beta(3) integrins. Abciximab is specific for platelet glycoprotein IIb/IIIa receptors, e.g., on blood cells. Human aortic smooth muscle cells express alpha (v)beta(3) integrins on their surface. Treating beta(3) expressing smooth muscle cells may prohibit adhesion of other cells and decrease cellular migration or proliferation, thus reducing restinosis following percutaneous coronary interventions (CPI) e.g., stenosis, angioplasty, stenting. Abciximab also inhibits aggregation of blood platelets.

In one case, the peptide can be a glycopeptide. "Glycopeptide" refers to oligopeptide (e.g. heptapeptide) antibiotics, characterized by a multi-ring peptide core optionally substituted with saccharide groups, such as vancomycin. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327; 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 4573-4590. Representative glycopeptides include those identified as A477, A35512, A40926, A41030, A42867, A47934, A80407, A82846, A83850 A84575, AB65, Actaplanin, Actinoidin, Ardacin, Avoparcin, Azureomycin, Balhimycin, Chloroorientiein, Chloropolysporin, Decaplanin, -demethylvancomycin, Bremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MMS6598, OA-7653, Orenticin, Parvodicin, Ristocetin, Ristomycin, Synmonicin, Teicoplanin, UK-68597, UK-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

In one facet, the peptide is a lipidated glycopeptide. The term "lipidated glycopeptide" refers specifically to those glycopeptide antibiotics which have been-synthetically modified to contain a lipid substituent. As used herein, the term "lipid substituent" refers to any substituent containing 5 or more carbon atoms, preferably, 10 to 40 carbon atoms. The lipid substituent may optionally contain from 1 to 6 heteroatoms selected from halo, oxygen, nitrogen, sulfur and phosphorous. Lipidated glycopeptide antibiotics are well-known in the art. See, for example, in U.S. Pat. Nos. 5,840,684, 5,843,889, 5,916,873, 5,919,756, 5,952,310, 5,977,062, 5,977,063, EP 667,353, WO 98/52589, WO 99/56760, WO 00/04044, WO 00/39156, the disclosures of which are incorporated herein by reference in their entirety.

Anti-inflammatory agents include, e.g., analgesics (e.g., NSAIDS and salicylates), antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference*, 2001 Edition. Specifically, the anti-inflammatory agent can include dexamethasone, which is chemically designated as (11β,16α)-9-fluoro-11,17,21-trihydroxy-16-methylpregna-1,4-diene-3,20-dione. Alternatively, the anti-inflammatory agent can include sirolimus (rapamycin), which is a triene macrolide antibiotic isolated from *Streptomyces hygroscopicus*.

Anti-platelet and anticoagulation agents include, e.g., Coumadin® (DuPont), Fragmin® (Pharmacia & Upjohn), Heparin® (Wyeth-Ayerst), Lovenox®, Normiflo®, Organ® (Organon), Aggrastat® (Merck), Agrylin® (Roberts), Ecotrin® (Smithkline Beechamn), Flolan® (Glaxo Wellcome), Halfprin® (Kramer), Integrillin® (COR Therapeutics), Integrillin® (Key), Persantine® (Boehringer Ingelheim), Plavix® (Bristol-Myers Squibb), ReoPro® (Centecor), Ticlid® (Roche), Abbokinase® (Abbtt), Activase® (Genentech), Eminase® (Roberts), and Strepase® (Astra). See, *Physician's Desk Reference*, 2001 Edition. Specifically, the anti-platelet and anti-coagulation agent can include trapidil (avantrin), cilostazol, heparin, hirudin, or ilprost.

Trapidil is chemically designated as N,N-dimethyl-5-methyl-[1,2,4]triazolo[1,-5-a]pyrimidin-4-amine. Cilostazol is chemically designated as 6-[4-(1-cyclohexyl-1H-tetrazol-5-yl)-butoxy]-3,4-dihydro-2(1H)-quinolinone.

Heparin is a glycosaminoglycan with anticoagulant activity; a heterogeneous mixture of variably sulfonated polysaccharide chains composed of repeating units of D-glucosamine and either L-iduronic or D-glucuronic acids. Hirudin is an anticoagulant protein extracted from leeches, e.g., Hirudo medicinalis. Iloprost is chemically designated as 5-[Hexahydro-5-hydroxy-4-(3-hydroxy-4-methyl-1-octen-6-ynyl)-2(1H)-pentalenylidene]pentanoic acid.

The immune suppressive agent can include, e.g., Azathioprine® (Roxane), BayRho-D® (Bayer Biological), CellCept® (Roche Laboratories), Imuran® (Glaxo Wellcome), MiCRhoGAM® (Ortho-Clinical Diagnostics), Neoran® (Novarts), Orthoclone OKT3® (Ortho Biotech), Prograf® (Fujisawa), PhoGAM® (Ortho-Clinical Diagnostics), Sandimmune® (Novartis), Simulect® (Novartis), and Zenapax® (Roche Laboratories). Specifically, the immune suppressive agent can include rapamycin or thalidomide. Rapamycin is a triene macrolide isolated from *Streptomyces hygroscopicus*.

Thalidomide is chemically designated as 2-(2,6-dioxo-3-piperidinyl)-1H-iso-indole-1,3(2H)-dione.

In one case, a therapeutically effective amount of the nitric oxide (NO) derivative compound binds to the functionally acid of the PEA. Examples of such compounds are 2,2,5,5-tetramethylpyrrolidine-1-oxy; 2,2,5,5-tetramethyl-3-pyrroline-1-oxy-3-carbonyl; 4-(N,N-dimethyl-N-hexadecyl)ammonium-2,2,6,6-tetramethylpiperidine-1-oxy, iodide (CAT16); 4-trimethylammonium-2,2,6,6-tetramethylpiperidine-1-oxy, iodide (CAT 1); 3-amino-2,2,5,5-tetramethylpyrrolidine-1-oxy; N-(3-(iodoacetyl)amino)-2,2,5,5-tetramethylpyrrolidine-1-oxy(PROXYL 1A); succinimidyl 2,2,5,5-tetramethyl-3-pyrroline-1-oxy-3-carboxylate; 2,2,5,5-tetramethyl-3-pyrroline-1-oxy-3-carboxylic acid; 2,2,6,6-tetramethylpiperidine-1-oxy; 4-amino-2,2,6,6-tetramethylpiperadine-1-oxy; 4-carboxy-2,2,6,6-tetramethylpiperadine-1-oxy; 4-acetamido-2,2,6,6-tetramethylpiperadine-1-oxy; 4-bromo-2,2,6,6-tetramethylpiperadine-1-oxy; 4-(N,N-dimethyl-N-(2-hydroxyethyl))ammonium-2,2,6,6-tetramethylpiperidine-1-oxy; 4-(N,N-dimethyl-N-(3-sulfopropyl)ammonium-2,2,6,6-tetramethylpiperidine-1-oxy; N-(4-(iodoacetyl)amino-2,2,6,6tetramethylpiperidine-1-oxy; N-(2,2,6,6-tetramethylpiperidine-1-oxy-4-yl)maleimide; and mixtures thereof. A particularly preferred compound is 4-amino-2,2,6,6-tetramethylpiperadine-1-oxy radical.

A niticoxide like compound can also be incorporated into the PEA. Suitable niticoxide like compounds are disclosed, e.g., in U.S. Pat. No. 5,650,447 and S-nitrosothiol derivative (adduct) of bovine or human serum albumin. See, e.g., Inhibition of neointimal proliferation in rabbits after vascular injury by a single treatment with a protein adduct of nitric oxide. David Marks et al *J. Clin. Invest.* (1995); 96:2630-2638.

An antimicrobial is a substance that kills or inhibits the growth of microbes such as bacteria, fungi, protozoals or viruses. The antimicrobial can be anti-viral, anti-bacterial, anti-fungal agent, or metal (e.g., Ag, Cu, or Hg). In a preferred aspect, the antimicrobial is not attached to the PEA. Rather, the antimicrobial is immersed within and around the PEA. In yet another embodiment, silver is a preferred antimicrobial.

The term growth factor refers to a naturally occurring protein capable of stimulating cellular growth, proliferation and cellular differentiation. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis). Examples of growth factors that can be used in accordance with the claimed invention include but are not limited to Endothelial growth factor (EGF), Erythropoietin (EPO), Fibroblast growth factor (FGF), Granulocyte-colony stimulating factor (G-CSF), Granulocyte-macrophage colony stimulating factor (GM-CSF), Growth differentiation factor-9 (GDF9), Hepatocyte growth factor (HGF), Insulin-like growth factor (IGF), Myostatin (GDF-8), Nerve growth factor (NGF), Platelet-derived growth factor (PDGF), Thrombopoietin (TPO), Transforming growth factor alpha(TGF-α), Transforming growth factor beta (TGF-β), Vascular endothelial growth factor (VEGF).

The PEAs of the present invention can also be reacted with other polymers. For example, when the PEA have pendant hydroxyl group, the functional groups can act as an alcohol and serve as the starting reactive site to chemically attach a synthetic absorbable aliphatic polyester macromolecule like poly-ε-caprolactone (PCL) or/and polylactide (PLA) (i.e., a PEA backbone with PCL or/and PLA grafted side chains).

In addition to being attached to or linked to one or more active materials, either directly or through a linker, PEAs of the present invention can be physically intermixed with one or more bioactive materials. As used herein, "intermixed" refers to a PEA of the present invention physically mixed with a bioactive and/or active material or a PEA of the present invention physically in contact with a bioactive and/or active material.

Any suitable amount of PEAs and bioactive material can be employed to provide a composition. The PEAs can be present in about 0.1 wt % to about 99.9 wt. % of the composition. Typically, the PEAs can be present above about 25 wt % of the composition; above about 50 wt % of the composition; above about 75 wt % of the composition; or above about 90 wt % of the composition.

A feature of this embodiment is reacting PEA with a polysaccharide, such as dextran, hyaluronic acid, chitosan, alginate, inulin, starch, cellulose, pullan, levan, mannan, chitin, xylan, pectin, glucuronan, laminarin, galactomannan, amylose, amylopectin, phytophtoorglucans, or ethylcellulose. Polysaccharides such as dextran, inulin, starch, cellulose, pullen, levan, mannan, chitin, xylan, pectin, glucuronan, laminarin, galactomannan, amylose, amylopectin, and phytophtoorglucans provide a hydroxy pendant functional group.

The PEA of the first embodiment can be reacted with the polysaccharide via a compound such as carbonyldiimidazole, which facilitates the reaction of $NH_2$ and COOH groups. For example, PEA compounds having a free $NH_2$ pendant functional group (e.g., PEA-Lys-25) can be reacted with a polysaccharide such a hyaluronic acid. Hyaluronic acid is a negatively charged polysaccharide and is as shown as follows:

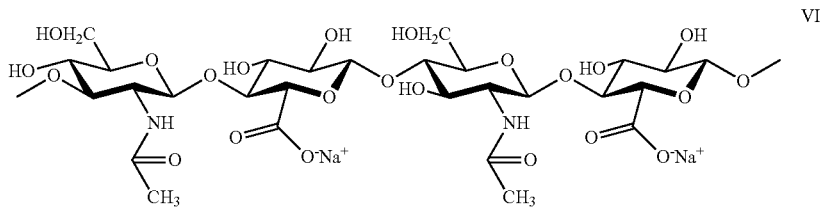

VI

In yet another facet of this embodiment, a gel is produced. Gels of this embodiment can be produced by several different methods.

In a first method for producing a gel, a PEA compound of formula I with free amine groups can be used to make gels via an amine-reactive bifunctional cross-linker. An amine-reactive bifunctional crosslinker (e.g., glutaraldehyde) is reacted with the PEA to form a gel. In addition to glutaraldehyde, dimethyl adipimidate (DMA), dimethyl suberimidate (DMS), dimethyl pimelimidate (DMP), N-hydroxysuccinimide (NHS) esters, dithiobis(succinimidylpropionate), and dithiobis(sulfosuccinimidylpropionate) DTSSP can be used.

In a second method for producing a gel, carbonyldiimidazole is used to facilitate the reaction of a free $NH_2$ pendant functional group with a free COOH functional group to form a gel. A PEA compound of formula I having a free pendant functional group of $NH_2$, or COOH is reacted with carbonyldiimidazole and a compound having a corresponding $NH_2$ or COOH functional group. For example, a PEA compound having a free amine group (e.g., PEA-Lys-25) can be reacted with PEA having carboxylic group (e.g., PEA-COOH-25) via carbonyldiimidazole to form a transparent gel.

In a yet another facet of this embodiment, a hydrogel can be produced. For example, in a method for producing a hydrogel, a photoinitiator is added to a dimethyl sulfoxide solution of PEA of formula I and PEG-DA with molecular weight 700. The weight ratio of PEA precursor to PEG-DA is from 0.1-0.3:1 and preferably is 0.2:1

Any photoinitiator can be used, but the photoinitiator is preferably 2,2-dimethoxy 2-phenyl acetophenone, 4-(2-hydroxyethoxy)phenyl-(2-hydroxy-2-propyl)ketone (Irgacure 2959) and DMPAP. The photoinitiator is preferably added in an amount of 0.01-10%, 0.1-3.0% (w/w). A solvent is optionally added depending on the type of photoinitiator used (e.g., DMPAP). The solvent solvent, e.g., N-methylpyrrolidone, tetrahydrofuran, dimethyl formamide or dimethyl sulfoxide, is added to the solution.

Photocrosslinking is carried out by UV irradiation, e.g., at room temperature, preferably 20° C. to 30° C., for 5 to 30 minutes, preferably 10 to 20 minutes. Unreacted chemicals are then preferably leached out of the resulting gel.

The hydrogels or gels produced with the PEAs are useful for a variety of purposes including the controlled release of bioactive and/or active materials. In this aspect, the bioactive and/or active materials may be reacted with the free functional groups in the PEAs to form covalent bonds between the bioactive and/or active materials and a precursor, and/or physically encapsulated or entrapped by the precursor. The bioactive and/or active material is released by metabolic action on the hydrogel, and the attachment to or entrapment in or encapsulation with hydrogel delays release, for example, for 2 to 48 hours or more.

The hydrogels or gels from the PEAs herein are also useful as a temporary skin cover, e.g., as a wound dressing or artificial skin. In this case, the hydrogel or gel can advantageously incorporate antimicrobial agent and/or would healing growth factor(s) as discussed above.

The hydrogels or gels produced from the PEAs herein can also encapsulate viruses used in gene therapy to protect the viruses from the body's immune system until they reach the site where the genetic alteration is to occur. In conventional gene therapy, viruses are injected at the site of prospective incorporation and many injections are required to accommodate for inactivation of viruses. The hydrogels herein protect the viruses so that fewer injections may be utilized.

The hydrogels from the PEAs herein can also be useful for agricultural purposes to coat seeds. The hydrogel coating promotes retention of water during seed germination and promotes oxygen transport via pore structures and may include chemical agents, e.g., pesticides, for delivery to the seeds.

The hydrogels from PEA herein are useful for the administration of basic fibroblast growth factor (bFGF) to stimulate the proliferation of osteoblasts (i.e., promote bone formation) and to stimulate angiogenesis (development of blood vessels). The pendant free carboxylic acid groups in the precursors herein serve as sites for the ionic bonding of bFGF. The hydrogels incorporating bFGF are applied to bone or blood vessels locally. Upon the biodegradation of the hydrogel, sustained release of bFGF for promoting bone growth and blood vessel formation is obtained. The bonding of the bFGF to the precursors herein protects the bFGF against enzymatic degradation or denaturing so the bFGF can perform its biological functions and occurs because of the bFGF's inherent affinity toward acid compounds.

The hydrogels from the PEAs herein can be useful for integral components in microdevices, for example, biosensors. The functional group in the hydrogel is very sensitive to various environmental stimuli, for example, pH and metal ions concentration, the swelling ratio and other properties of the hydrogel can accordingly change based on the change of controlled external stimuli.

The hydrogels from the PEAs herein are also useful in the cases where hydrogels are conventionally used, e.g., for thickening in foods, for moisture release to plants, for fluid uptake and retention in the sanitary area, as hydrophilic coatings for textile applications, for contact lenses and for separation and diffusion gel in chromatography and electrophoresis.

The drugs, bioactive and/or active material in one facet of this embodiment are not reactive with components of the hydrogel-forming system herein and can be physically entrapped within the hydrogel or physically encapsulated within the hydrogel by including them in the reaction mixture subjected to photocrosslinking so that the photocrosslinking causes formation of hydrogel with bioactive and/or active material entrapped therein or encapsulated thereby.

The foregoing description of the invention has been presented describing certain operable and preferred embodiments. It is not intended that the invention should be so limited since variations and modifications thereof will be obvious to those skilled in the art, all of which are within the spirit and scope of the invention.

Working examples for the invention are set forth below.

EXAMPLE 1

Synthesis of PEA with Pendant Amine Groups

PEA polymers with pendant amine groups were synthesized from the following five major steps: (1) synthesis of protected $\epsilon$-(benzyloxycarbonyl)-L-lysine N-carboxyanhydride (Z-LysNCA), (2) synthesis of di-p-toluenesulfonic acid salts of bis-L-phenylalanine ester (Phe-6) and its derivative monomer with Z-LysNCA (Z-Lys-Phe-6); (3) synthesis of di-p-nitrophenyl esters of dicarboxylic acids (NS); (4) solution polycondensation of monomers Z-Lys-Phe-6 and NS; and (5) deprotection of the resulting polymer (PEA-Z-Lys).

Synthesis of Di-p-toluenesulfonic Acid Salt of Bis-L-phenylalanine Hexane-1,6-diester Monomer (Phe-6)

Phe-6 was produced directly condensing phenylalanine (42.95 g, 0.26 mol), 1,6-hexanediol (14.20 g, 0.12 mol) with refluxed toluene (500 mL) in the presence ofp-toluenenesulfonic acid monohydrate (57.00 g, 0.30 mol). The heterogeneous solid-liquid reaction mixture was heated to 120° C. and reflux for 24 hrs until 14.90 mL (0.83 mol) of water collected by Dean-Stark apparatus. The resulting reaction mixture was cooled down to room temperature. The precipitate was filtered on a Buchner funnel and then purified by recrystallizing three times in water, filtered again and dried in vacuo. Yield: 68%.

Synthesis of $\epsilon$-(benzyloxycarbonyl)-L-lysine N-carboxyanhydride (Z-LysNCA)

The synthesis of $\epsilon$-(benzyloxycarbonyl)-L-lysine N-carboxyanhydride was prepared by a Fuchs-Farthing method using triphosgene. A suspension of H-Lys(Z)—OH (6.00 g, 21.40 mmol) in 150 mL of ethyl acetate was refluxed in a nitrogen atmosphere. A solution of triphosgene (2.37 g, 8.00 mmol) dissolved in 30 mL ethyl acetate was added to the stirred reaction mixture. When the reaction mixture became transparent, a stream of nitrogen was bubbled through the solution to remove HCl. After the reaction was complete, the solvent was evaporated under vacuum to give a colorless oily residue which crystallized upon cooling in a refrigerator. For further purification of the Z-LysNCA obtained, it was recrystallized three times in a mixture of ethyl acetate/petroleum ether and dried in vacuo. The yield was 87%.

Synthesis of Amine protected Di-p-toluenesulfonic Acid Salt of N-benzyloxycarbonyl-L-lysnyl-bis-L-phenylalanine Hexane-1,6-diester Monomer (Z-Lys-Phe-6)

The amount of Z-LysNCA monomer to be incorporated into PEA depends on the desired content of the amine groups on the final PEA polymer, which can be controlled via the molar ratio of Phe-6 to Z-LysNCA. The different molar combinations of Phe-6 and Z-LysNCA are summarized in Table 1 and illustrated in Scheme 1 below. Z-LysNCA (2.43 g, 7.93 mmol) was added to a solution of Phe-6 (6.00 g, 7.93 mmol) in 30 mL of N,N-dimethylacetamide (DMA). The reaction mixture was stirred at 40° C. for 3 hrs and the solution temperature was raised to 80° C. for 24 hrs in a nitrogen atmosphere. The reaction was subsequently cooled to a room temperature and used in the next stage polycondensation reaction without further purification.

Synthesis of Di-p-nitrophenyl Sebacate Monomer (NS)

Di-p-nitrophenyl sebacate was prepared by reacting sebacoyl chloride with p-nitrophenol. A solution of p-nitrophenol (43.00 g, 0.31 mol) and triethylamine (43.13 mL, 0.31 mol) dissolved in 500 mL acetone was placed in a single-neck round-bottom flask equipped with magnetic stirrer and a dropping funnel. The contents of the flash were kept at 0° C. by cooling with an ice/water mixture. Sebacoyl chloride (28.54 mL, 0.13 mol) in 100 mL of acetone was then added dropwise into the chilled solution while stirring for three hours and at room temperature overnight. The resulting NS was precipitated in distilled water, dried in vacuum at room temperature and then purified by recrystallization from ethyl acetate three times. Yield: 75%.

The synthesis of Phe-6, NS and Z-Lys-Phe-6 is depicted as follows:

Scheme 2

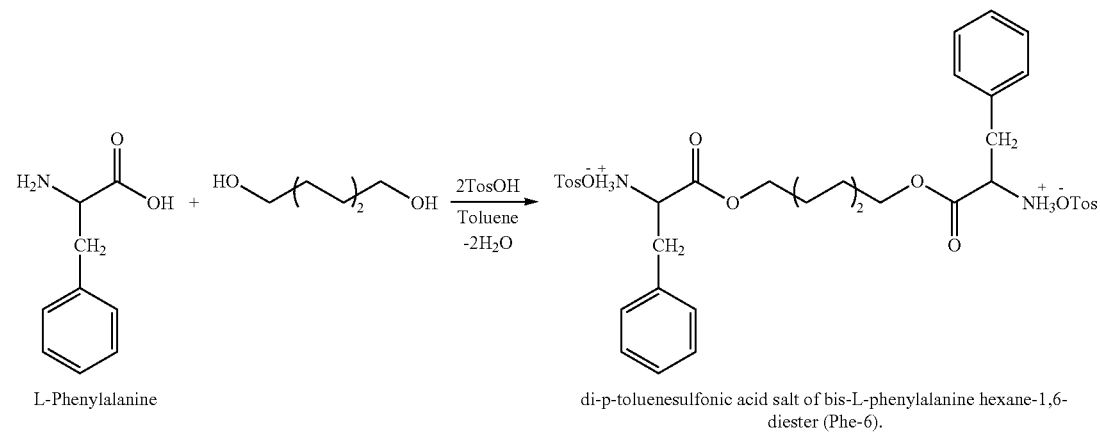

L-Phenylalanine di-p-toluenesulfonic acid salt of bis-L-phenylalanine hexane-1,6-diester (Phe-6).

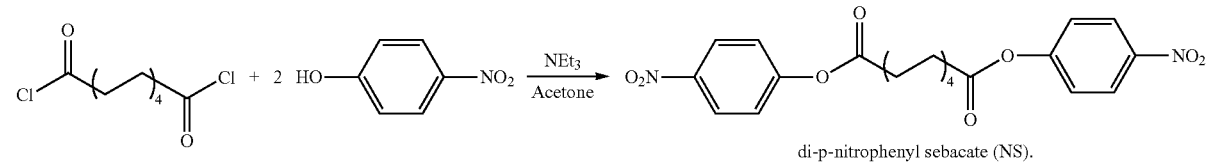

di-p-nitrophenyl sebacate (NS).

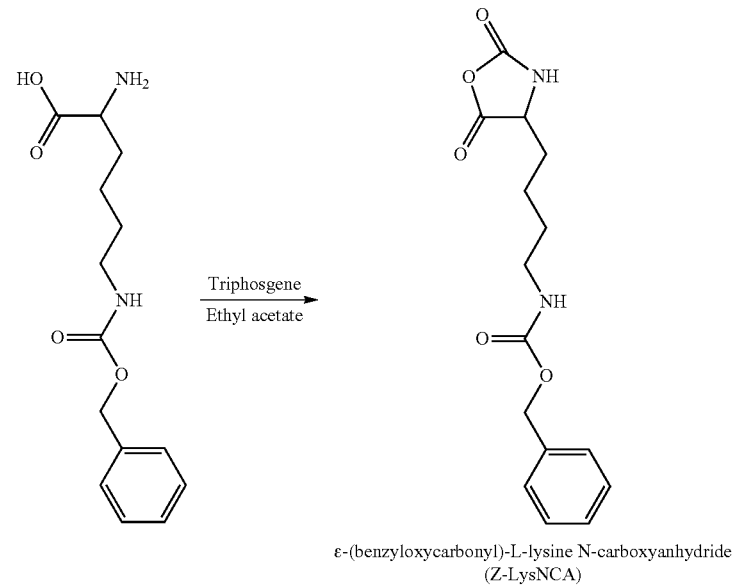

ε-(benzyloxycarbonyl)-L-lysine N-carboxyanhydride (Z-LysNCA)

-continued

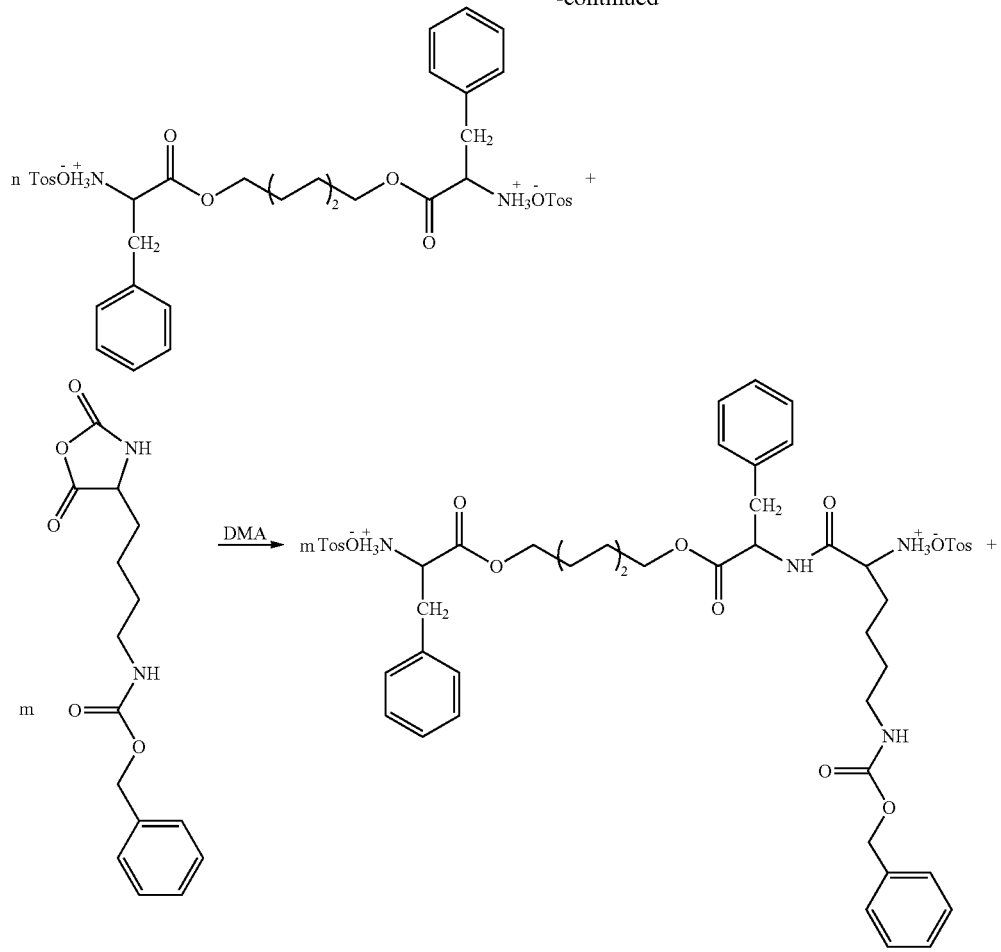

N-benzyloxycarbonyl-L-lysnyl-bis-L-phenylalanine Hexane-1,6-diester (Z-Lys-Phe-6)

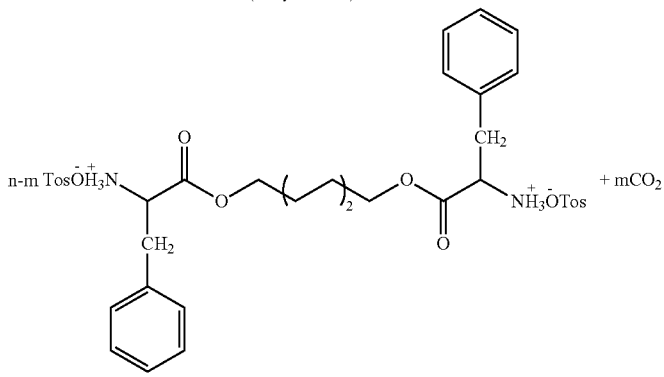

Synthesis of Amine-protected poly(ester amide)s, PEA-Z-Lys

Synthesis of PEA-Z-Lys-50 (see sample 6 in Table 1 below) is exemplified by the following synthesis procedures. NS (3.52 g, 7.93 mmol) and dry NEt$_3$ (2.41 mL, 17.45 mmol) were added to a solution of Z-Lys-Phe-6-50 (8.08 g, 7.93 mmol) in 30 mL of DMA under nitrogen atmosphere. The reaction solution was stirred at room temperature for 5 min and subsequently at 80° C. for 24 hrs. The resulting solution was cooled to room temperature, diluted with 30 ml of DMA and precipitated into an excess of cold ethyl acetate. Purification was performed by dissolving the polymer in dichloromethane and slowly adding into an excess of cold ethyl acetate. The tar-like polymer was filtered off, and dried in vacuo at 50° C. The composition of PEA-Z-Lys was determined by $^1$H and $^{13}$C NMR in DMSO-d$_6$. This polymer was used for the preparation of deprotected PEA-Lys-NH$_2$.

Synthesis of Amine-pendant poly(ester amide)s, PEA-Lys-NH$_2$

The protective groups (Z groups) of the side-chain amine groups in the Lys unit were removed by utilizing trifluoroacetic acid/methanesulfonic acid/anisole mixture. The PEA-Z-Lys-50 (5.00 g) was dissolved in 20 mL of trifluoroacetic acid and stirred for 1 hr at room temperature. Subsequently, methanesulfonic acid of 1.30 mL was dissolved in 2.60 mL of anisole and added to the solution of PEA-Z-Lys-50. After stirring for an additional 1 hr, the solution was precipitated into an excess of cold diethyl ether. In order to remove the excess acids, the polymer was dissolved in DMA and neutralized with triethylamine and then precipitated into an excess of ethyl acetate. The resultant polymer was filtered off, and dried in vacuo at 50° C.

The reaction is shown as follows:

Scheme 3

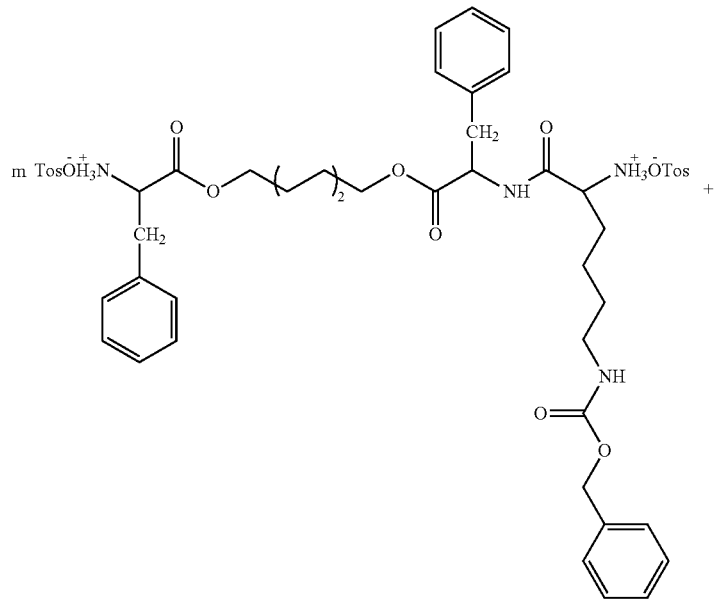

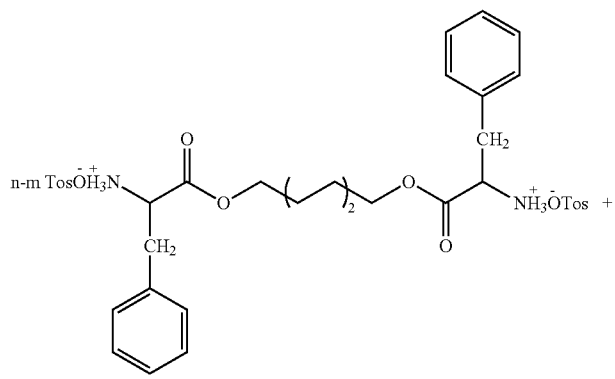

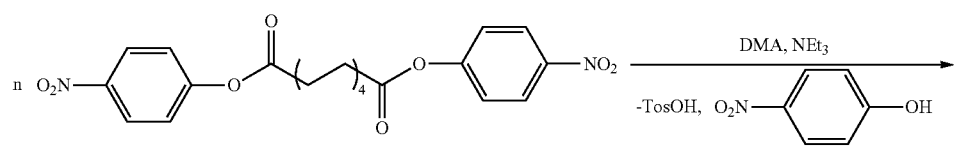

-continued

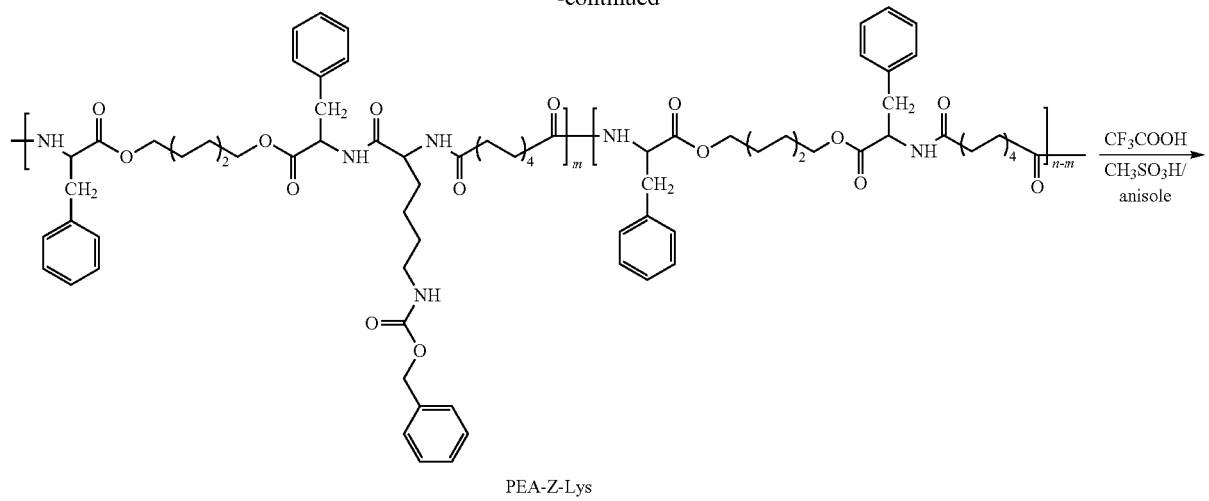

PEA-Z-Lys

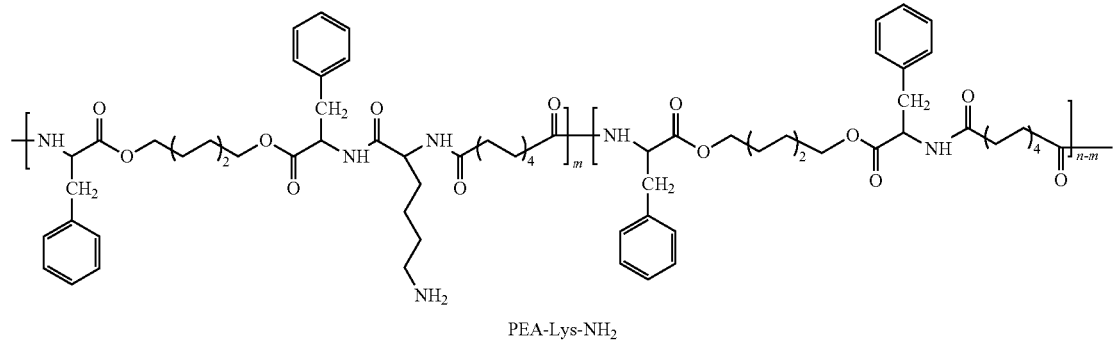

PEA-Lys-NH₂

The monomer combinations for the PEA-Z-Lys and PEA-Z-Lys-NH₂ syntheses are as follows:

TABLE 1

| Monomer Feed Ration | | | Expected | | | |
|---|---|---|---|---|---|---|
| Z-LysNCA | Phe-6 | NS | Z-Lysine content (%) | Z-Lys-Phe-6 | Protected Polymer | Deprotected Polymer |
| 0 | 1 | 1 | 0 | Z-Lys-Phe-6-0 | PEA-Z-Lys-0 | |
| 1 | 19 | 19 | 5 | Z-Lys-Phe-6-05 | PEA-Z-Lys-05 | PEA-Lys-NH₂-05 |
| 1 | 5.7 | 5.7 | 15 | Z-Lys-Phe-6-15 | PEA-Z-Lys-15 | PEA-Lys-NH₂-15 |
| 1 | 3 | 3 | 25 | Z-Lys-Phe-6-25 | PEA-Z-Lys-25 | PEA-Lys-NH₂-25 |
| 1 | 1.9 | 1.9 | 35 | Z-Lys-Phe-6-35 | PEA-Z-Lys-35 | PEA-Lys-NH₂-35 |
| 1 | 1 | 1 | 50 | Z-Lys-Phe-6-50 | PEA-Z-Lys-50 | PEA-Lys-NH₂-50 |

Fluorescent Dye Attachment, PEA-Lys-Dye

A fluorescent dye is attached onto the free amine site of PEA-Lys-NH$_2$-05 to demonstrate the existence and usefulness of pendant amine groups on the PEA polymer chain. A fluorescent dye-tagged PEA (PEA-Lys-NH$_2$-05-Dye) is produced. A solution of PEA-Lys-NH$_2$-0.5 (1.00 g) and NHS—fluorescein dye (10 mg) in 15 ml DMSO were stirred at room temperature. After 6 hrs, the solution was precipitated into distilled water. The polymer was sequentially washed with distilled water to remove any physically absorbed fluorescent dye and dried in vacuo overnight. The dried polymer (0.10 g) was dissolved in 10 mL chloroform, and the solution was cast onto glass cover slides. The coated slides were dried in vacuo for 12 hrs and used for fluorescent testing.

The reaction is illustrated as follows:

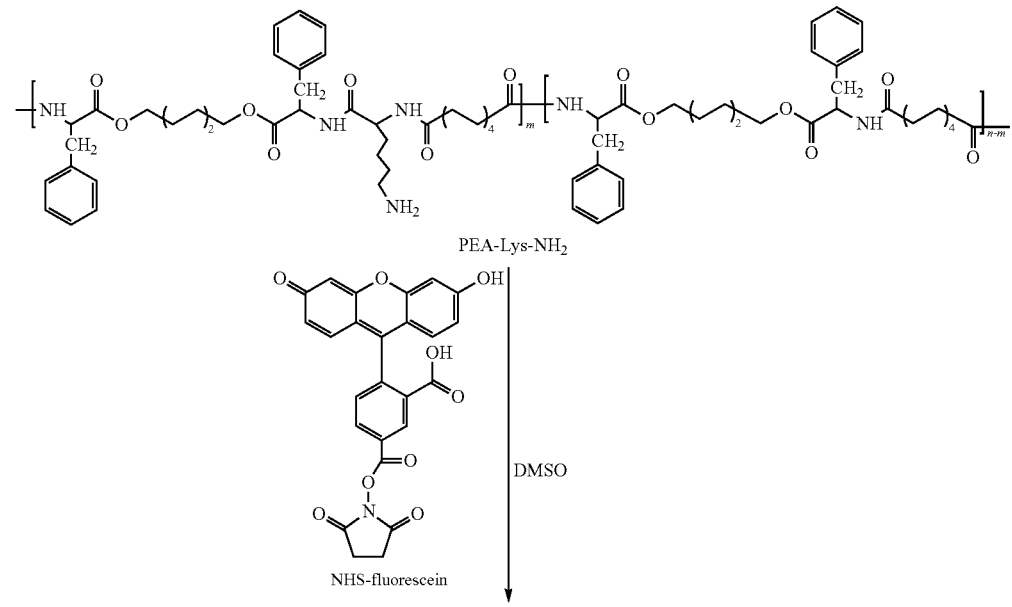

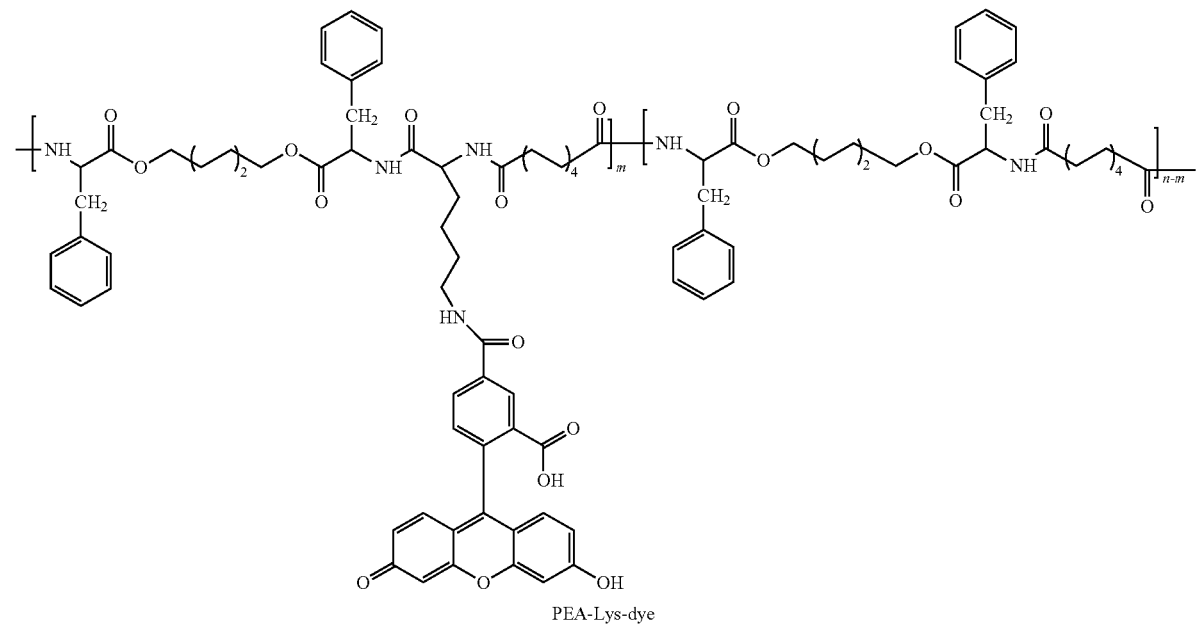

Characterization

1H NMR and $^{13}$C NMR Spectra were recorded on Varian (Palo Alto, Calif.) Unity Inova 400-MHz Spectrometer, with the residual proton resonance or the carbon signal of the deuterated solvent as the internal standard. The number-average and weigh-average molecular weight of the resultant polymers were determined with a Waters 410 size-exclusion chromatography equipped with two Waters Styragel columns (HT6E, HT3) and a differential refractometer detector. Chloroform was used as the eluent (1.0 mL/min) and the average molecular weight of the polymers was calculated based on calibrations using polystyrene standards. Infrared spectra were recorded with a PerkinElmer (Madison, Wis.) Nicolet Magana 560 FTIR spectrometer, using KBr plates. The NHS-fluorescein attached PEA sample was examined with Olympus BX41 fluorescent microscope. The thermal properties of the monomers and polymers were analyzed with a TA Instruments DSC 2920 differential scanning calorimenter (TA Instruments, New Castle, Del.). DSC samples were analyzed over the temperature range −42-270° C. with a scan rate of 10° C./min. The reduced viscosity of the resultant polymers was determined with a Cannon-Ubbelohde viscometer in DMSO solution at a concentration of 0.25 g/dL at 25° C.

Cell Culture

Bovine Endothelial Aorta Cells (BAEC, primary cells) from VEC Technologies were maintained at 37° C. in 5% $CO_2$ in Medium 199 (Invitrogen, Carlsbad, Calif.) supplemented with 10% Fetal Clone 111 (HyClone, Logan, Utah), and 1% each of penicillin-streptomycin, MEM amino acids (Invitrogen, Carlsbad, Calif.), and MEM vitamins (Mediatech, Manassas, Va.). BAECs were used from passages 8-12. Media was changed every 2 days. Cells were grown to 70% confluence before splitting or harvesting.

Cell Adhesion and Proliferation Assay

The evaluation of the cell attachment capability on the polymer surface and polymer cytotoxicity in the media were performed by cell proliferation assay with subsequent MIT assay. The round micro cover glasses (diameter, 12 mm, no. 2, VWR, West Chester, Pa.) were coated with polymer by dipping the glass into the polymer/DMF solution (5 wt %) and vacuum drying. This coating and drying procedures were repeated for three times. After the final vacuum drying, the PEA-Lys-NH$_2$-25 coated glass coverslips were placed into cell culture plates. Cell culture plates treated with 2 wt % gelatin aqueous solution and the non treated wells were used as controls.

Cultured cells were seeded onto each test well with exact same amount at an appropriate cell density concentration (20,000 cells/well) in 24-well plates and then incubated in an incubator. Cell media was changed every day. After the predetermined incubation times (24 hrs, 48 hrs, 72 hrs), the cell culture plates were removed from the incubator. The media from the wells was then aspirate, and 0.5 ml fresh media was added to each well. After that, 40 µl of MTT solution (5 mg/ml) was subsequently added to each well, followed by 4 hr incubation at 37° C., 5% $CO_2$. The cell culture medium was carefully removed and 400 µL of acidic isopropyl alcohol (with 0.1 M HCl) was added to dissolve the formed formazan crystal. The plate was slightly shaked for 30 mins and 100 uL solution was transferred from each well to a 96 well plate. Optical density (OD) of each well was measured at 570 nm (subtract background reading at 690 nm) by using a microplate reader.

Results

Figure 1B:
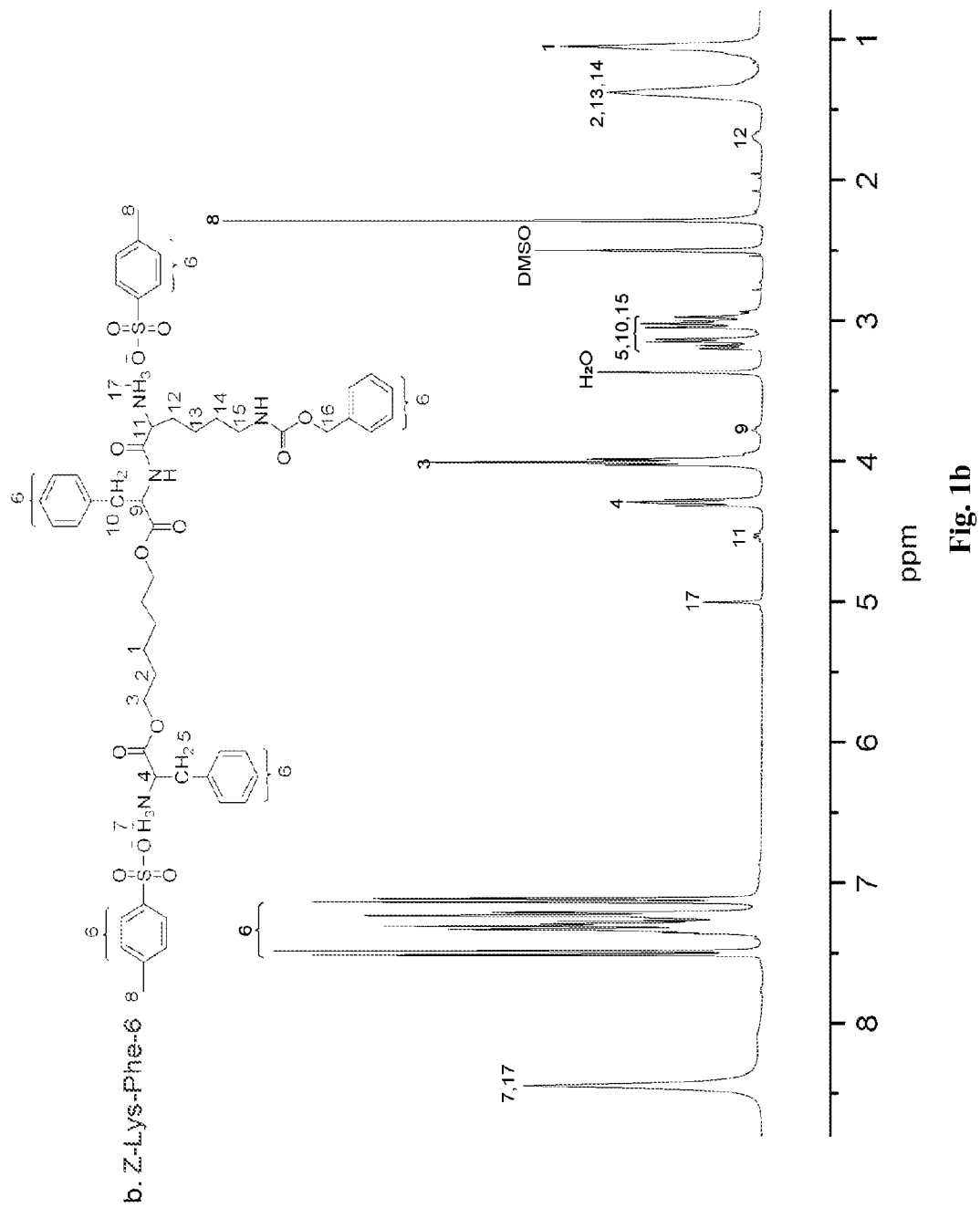
Figure 2A:
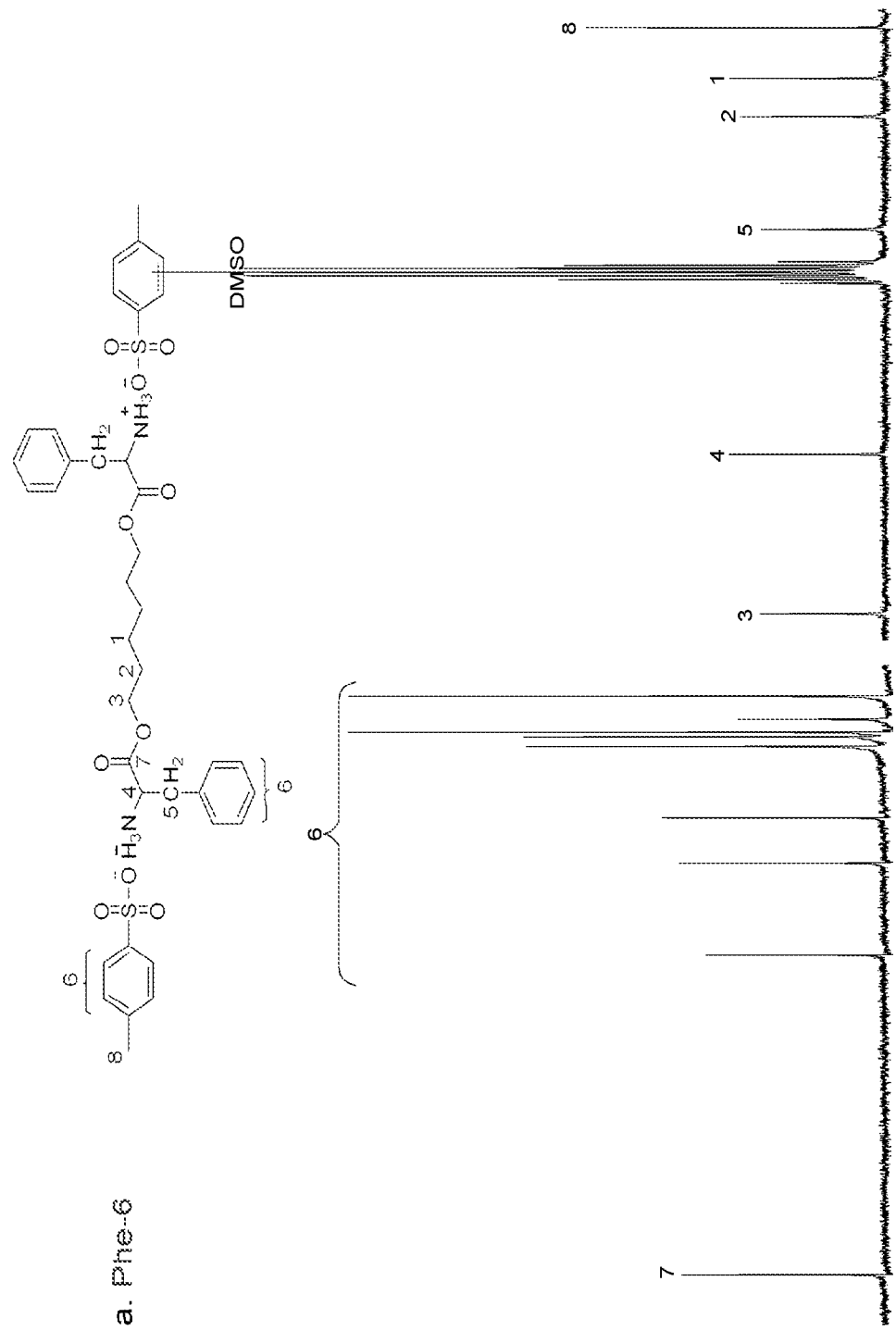
FIG. 2 illustrates an $^{13}$C NMR spectra of two monomers (a) Phe-6 and (b) Z-Lys-Phe-6.
Figure 2B:
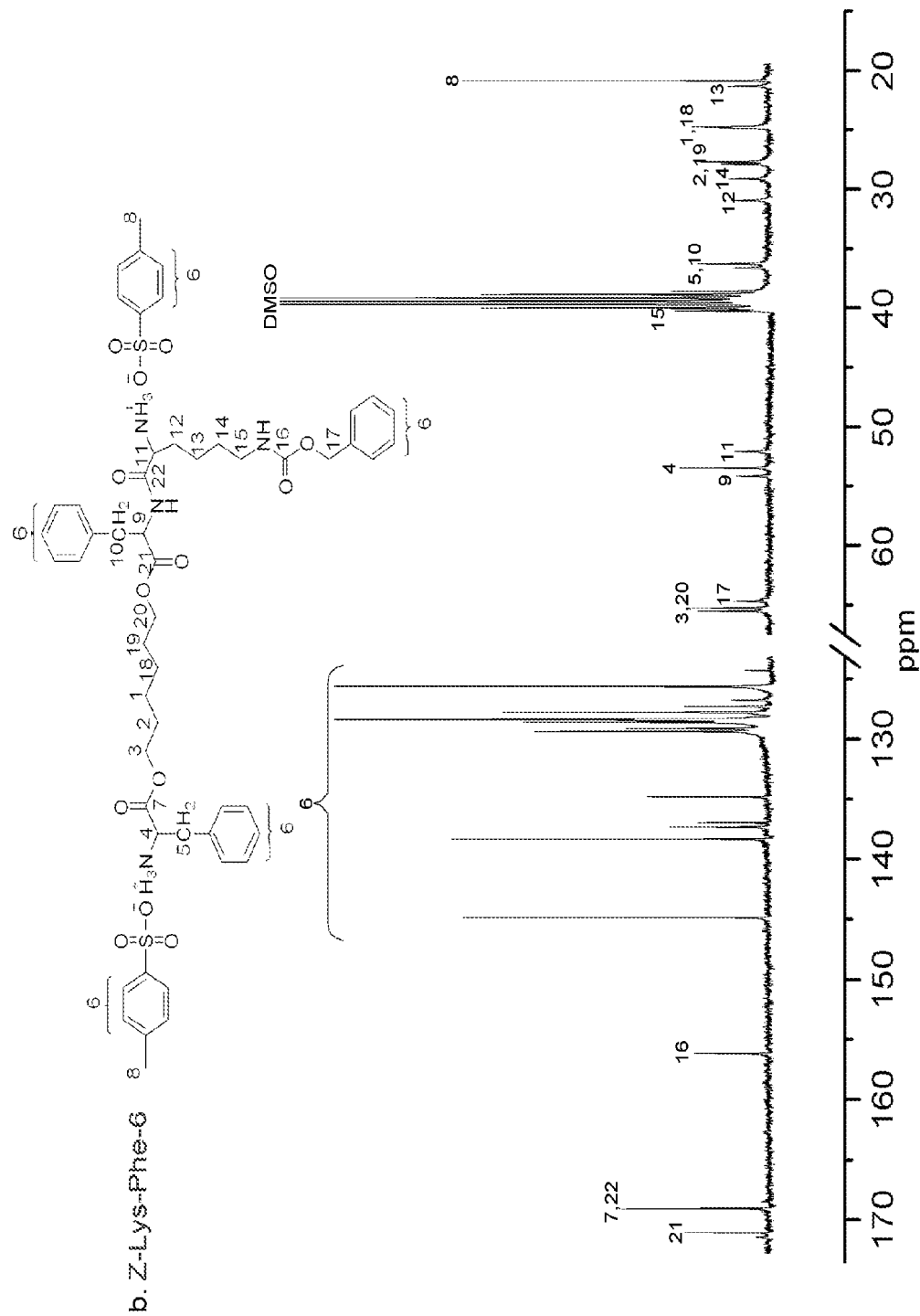

The structure of the Z-Lys-Phe-6 was confirmed by $^1$H NMR and $^{13}$C NMR. The $^1$H NMR peaks marked with numbers from 1 to 18 are assigned to the corresponding protons of Z-Lys-Phe-6 and Phe-6 as shown in FIG. 1. When comparing with the $^1$H NMR of Phe-6, the distinct peak at 5.00 ppm on the spectrum of Z-Lys-Phe-6 was assigned to the ArCH$_2$ protons derived from the protecting group of Lysine segment. An identical observation was made in the $^{13}$C NMR spectra (FIG. 2.) which showed the peak at 64.67 ppm corresponding to the carbon atoms of ArCH$_2$. In the carbonyl region, the peaks at 156.15, 169.00, 169.09 and 171.06 ppm were attributed to the different carbon of C=O from phenylalanine and Lysine segments. The existence of Lysine segment has broken the symmetrical structure of methylene carbons of diol part and every methylene carbons shown two splitted peaks in $^{13}$C NMR spectrum of Z-Lys-Phe-6.

The degree of incorporating Z-Lysine segments per Phe-6 molecule was calculated from the ratio of integration value of 5.00 ppm assigned to methylene proton signal of Z group to that of 4.00 ppm assigned to methylene proton signal of Phe-6 in the $^1$H NMR spectrum. As a result, the level of Z-Lysine unit incorporated into Phe-6 unit in Z-Lys-Phe-6 monomer could be quantitatively controlled by changing the feeding molar ratio of Phe-6 and Z-LysNCA reactants (see Table 1).

Synthesis of PEA-Z-Lys

As shown in Scheme 3, the amine-protected PEA-Z-Lys were prepared by solution polycondensation of Z-Lys-Phe-6 and Phe-6 with NS monomers. The polycondensation proceeded provided a high yield of PEA-Z-Lys. In this polymerization reaction, triethylamine was used as an acid receptor for toluenesulfonic acid which was produced during the regeneration of amino groups from the Z-Lys-Phe-6 and Phe-6 monomers. NS is a stable and solid monomer, therefore, the stoichiometric balance of amine and carboxyl groups in polycondensation can be controlled by utilizing accurately weighted monomers.

Table 2 shows the polymerization yields and the $\eta_{red}$ of PEA-Z-Lys as follows:

TABLE 2

| Polymer | Yield (%) | Lysine molar ratio (Mol %)$^a$ | $M_n$ (kg/mol)$^b$ | $M_w$ (kg/mol)$^c$ | $M_w/M_n$ | $\eta_{red}$ (g/dL)$^d$ | $T_g$ (° C.) |
|---|---|---|---|---|---|---|---|
| PEA-Z-Lys-0 | 82 | — | 68.0 | 89.9 | 1.32 | 0.58 | 32.35 |
| PEA-Z-Lys-05 | 79 | 2 | 67.0 | 104.0 | 1.55 | 0.58 | 28.95 |
| PEA-Lys-NH$_2$-05 | 78 | — | 45.3 | 80.0 | 1.77 | 0.54 | 30.95 |
| PEA-Z-Lys-15 | 76 | 10 | 69.5 | 99.9 | 1.44 | 0.55 | 23.87 |
| PEA-Lys-NH$_2$-15 | 75 | — | 23.6 | 48.9 | 2.07 | 0.59 | 25.42 |
| PEA-Z-Lys-25 | 77 | 25 | 44.1 | 73.0 | 1.66 | 0.45 | 19.85 |
| PEA-Lys-NH$_2$-25 | 75 | — | 12.0 | 19.5 | 1.38 | 0.75 | 32.39 |
| PEA-Z-Lys-35 | 73 | 33 | 47.4 | 95.6 | 2.02 | 0.48 | 24.37 |

TABLE 2-continued

| Polymer | Yield (%) | Lysine molar ratio (Mol %)[a] | $M_n$ (kg/mol)[b] | $M_w$ (kg/mol)[c] | $M_w/M_n$ | $\eta_{red}$ (g/dL)[d] | $T_g$ (° C.) |
|---|---|---|---|---|---|---|---|
| PEA-Lys-NH$_2$-35 | 72 | — | 10.7 | 18.4 | 1.71 | 0.79 | 28.74 |
| PEA-Z-Lys-50 | 69 | 46 | 48.7 | 92.0 | 1.89 | 0.50 | 20.44 |
| PEA-Lys-NH$_2$-50 | 70 | — | — | — | — | — | 29.78 |

[a]Lysine molar ration in polymer determined by 1H NMR.
[b]Mn determined by GPC.
[c]Mw determined by GPC.
Measured in DMSO at 25° C. (concentration = 0.25 g/dL).

All the PEA-Z-Lys obtained were solid and insoluble in methanol but soluble in common organic solvent like chloroform, DMF and TI-IF.

Figure 3:
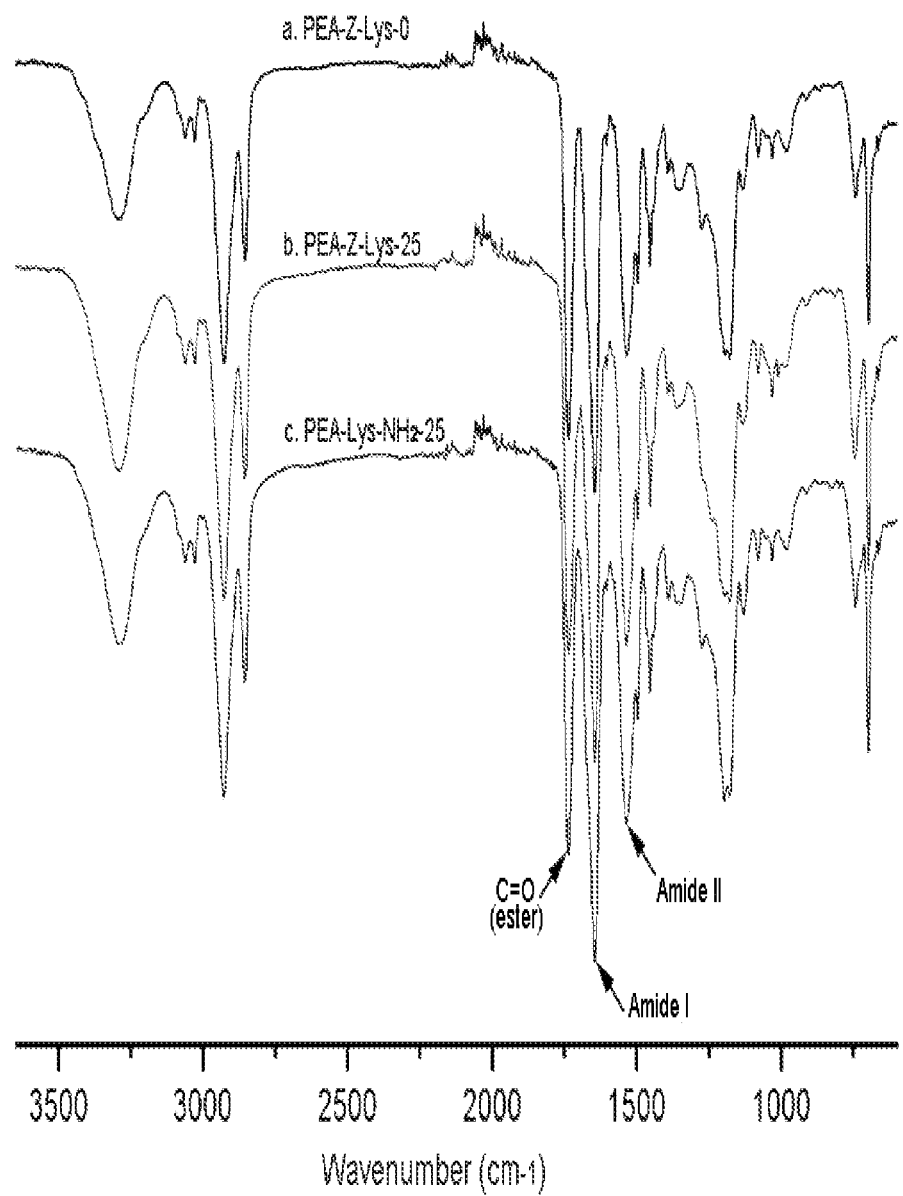
FIG. 3 shows an FTIR spectra of three representative PEAs (a) PEA-Z-Lys-O, (b) PEA-Z-Lys-25, and (c) PEA-Lys-NH$_2$-25.

Both FTIR and NMR confirmed the structure of the amine-protected PEA-Z-Lys polymer. The FTIR spectrum of PEA-Z-Lys-25, shown in FIG. 3, had the ester carbonyl stretch (1737 cm$^{-1}$), amide I bond (1644 cm$^{-1}$) and amide II bond (1534 cm$^{-1}$). In the $^1$H spectrum (FIG. 4), the distinct peaks assigned to the methyllene groups of protecting group of Lysine segments can be still observed at 5.00 ppm.

FIG. 5 shows a comparison of carbonyl region of the $^{13}$C NMR Spectrum for both the PEA-Z-Lys-0 (without Lysine segments) and the PEA-Z-Lys-25. The peaks at 171.67 ppm and 172.27 ppm are associated with the (Phe)CONH and (Phe)COO, respectively. The three additional peaks observed in the carbonyl region are attribute to (Z-Lys)CONH, (Z-Lys)COO and Z group at 171.33 ppm, 171.98 ppm and 156 ppm, respectively. These FTIR and NMR spectra confirm the presence of Z-Lys unit on the PEA-Z-Lys backbone. The GPC data of polymers is summarized in Table 2. All of PEA-Z-Lys polymers have a similar molecular weight and molecular weight distribution. The GPC traces are unimodal with no signal of coexisting low or high molecular weight species that may be produced from uncontrolled polycondensation. The composition of the PEA-Z-Lys, determined by $^1$H NMR, in some cases deviates slightly from intended composition (Table 2). The deviation is more pronounced at a lower LysNCA unit content. This is believed to be the results of removing lower molecular weight polymers having high Lysine content during the purification process.

Deprotection of PEA-Z-Lys

Figure 4A:
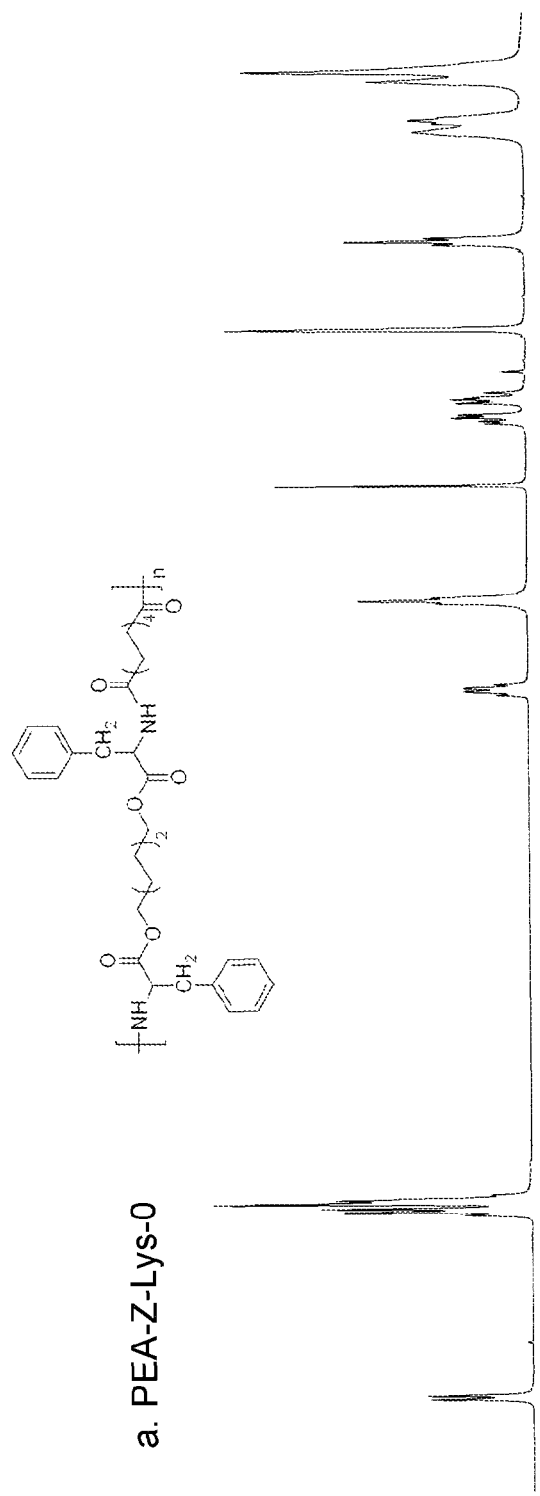
FIG. 4 is an $^1$H NMR spectra of three representative PEAs (a) PEA-Z-Lys-O, (b) PEA-Z-Lys-25, and (c) PEA-Lys-NH$_2$-25.
Figure 4B:
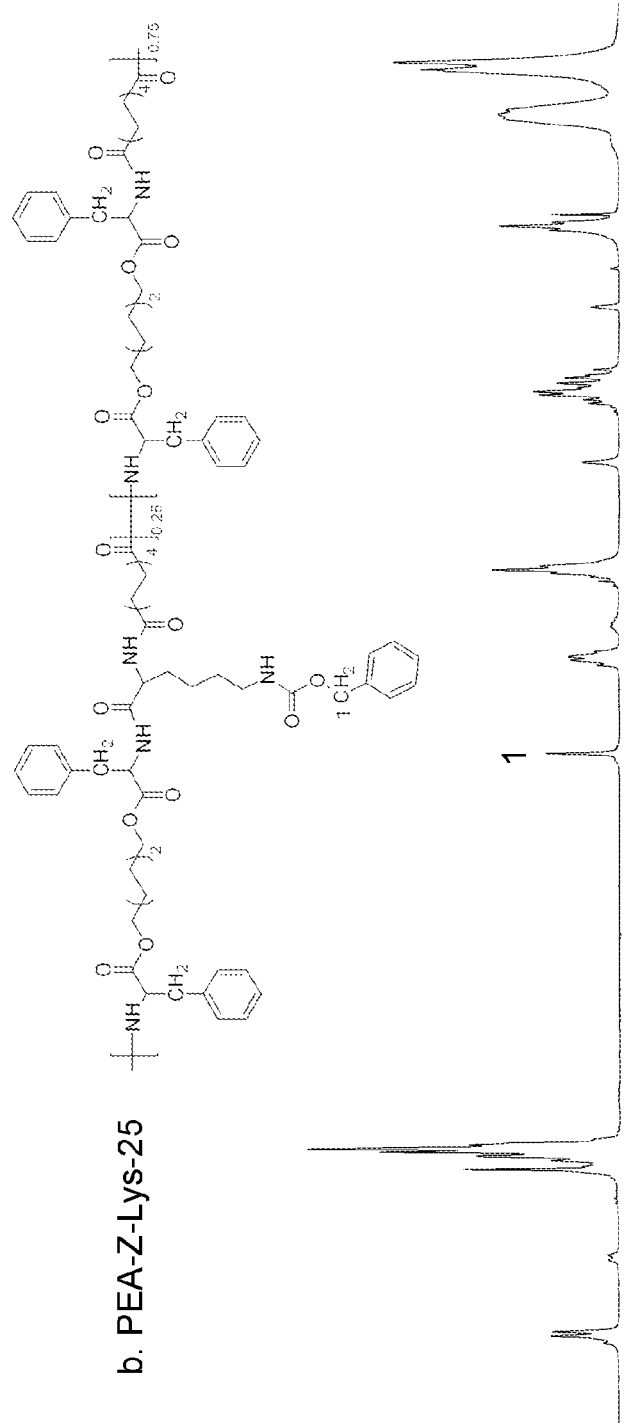
Figure 4C:
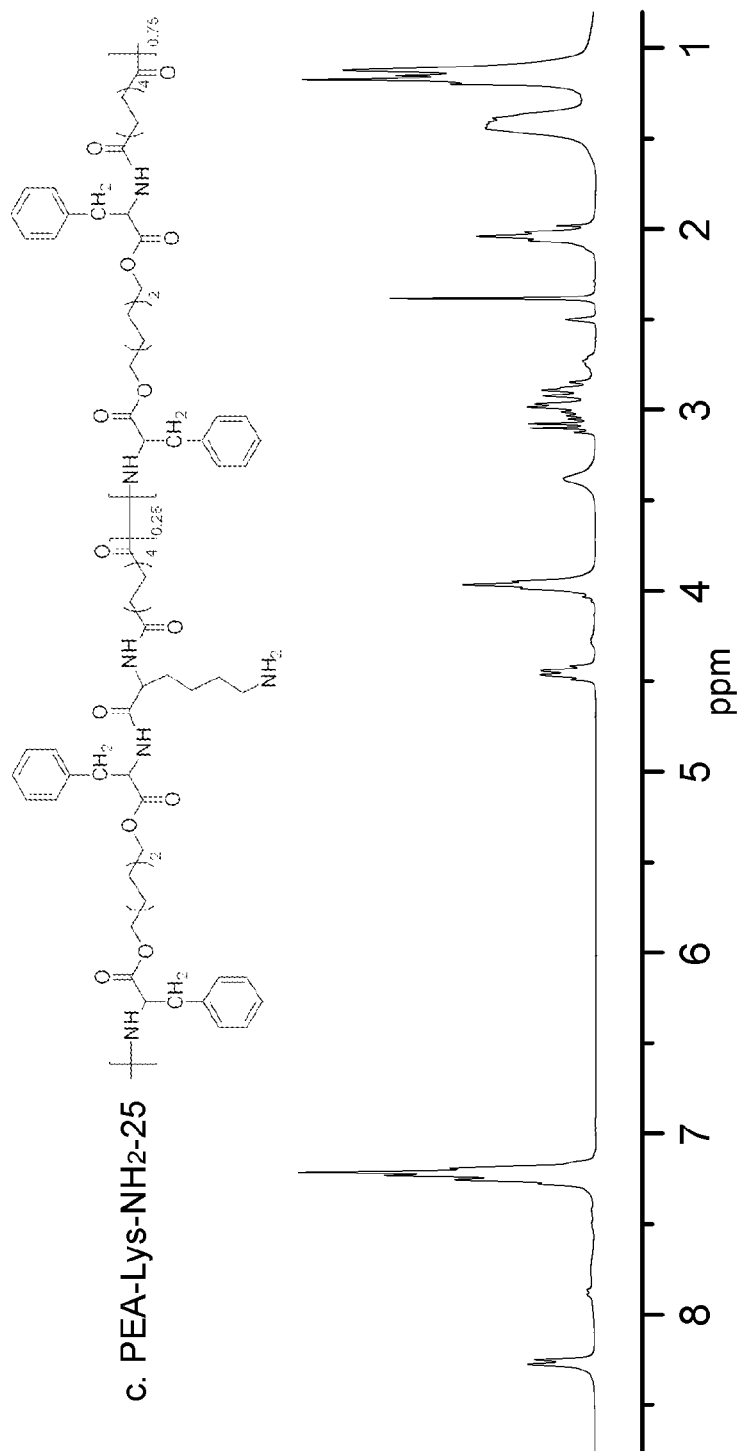
Figure 5A:
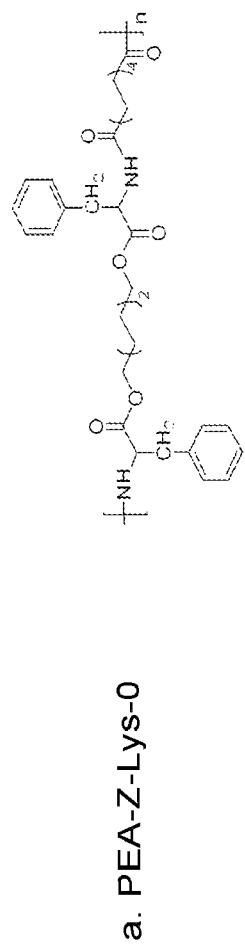
FIG. 5 illustrates an $^{13}$C NMR spectra of three representative PEAs (a) PEA-Z-Lys-0, (b) PEA-Z-Lys-25, and (c) PEA-Lys-NH$_2$-25.
Figure 5A:
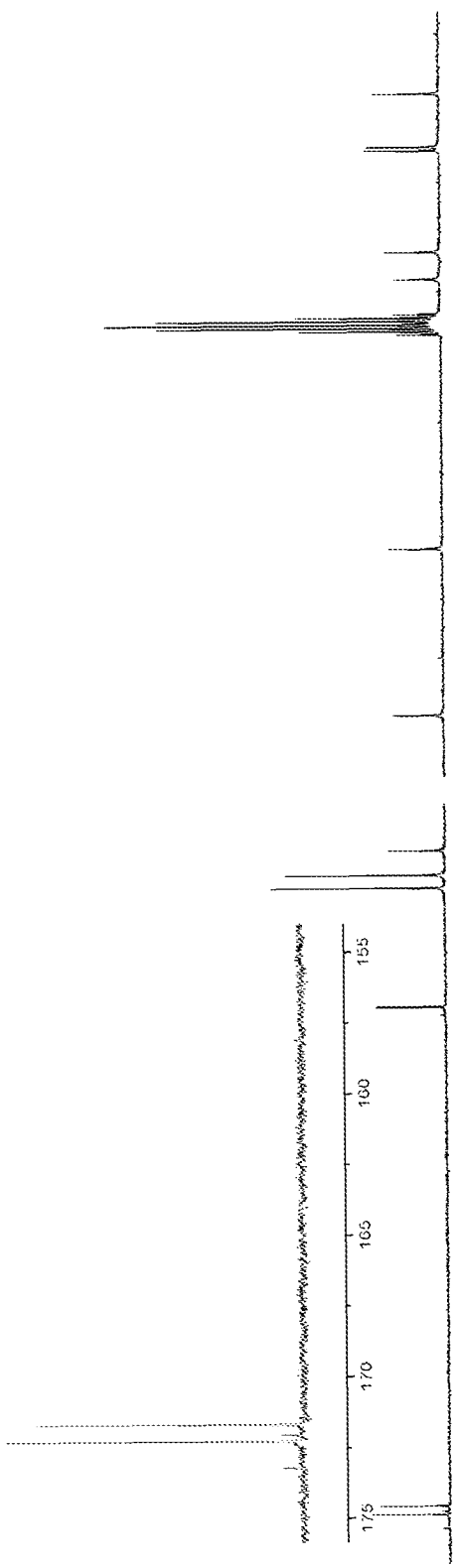
Figure 5B:
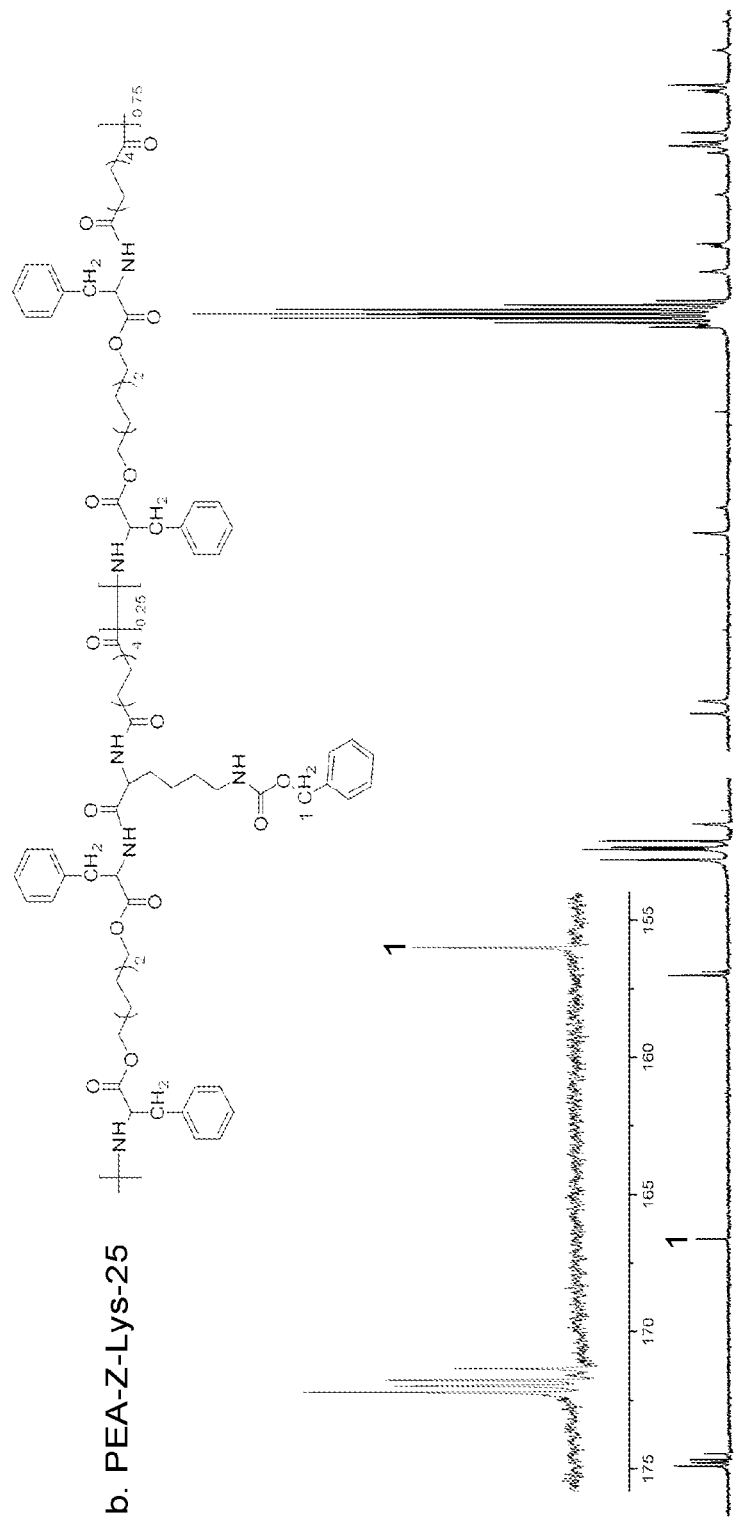
Figure 5C:
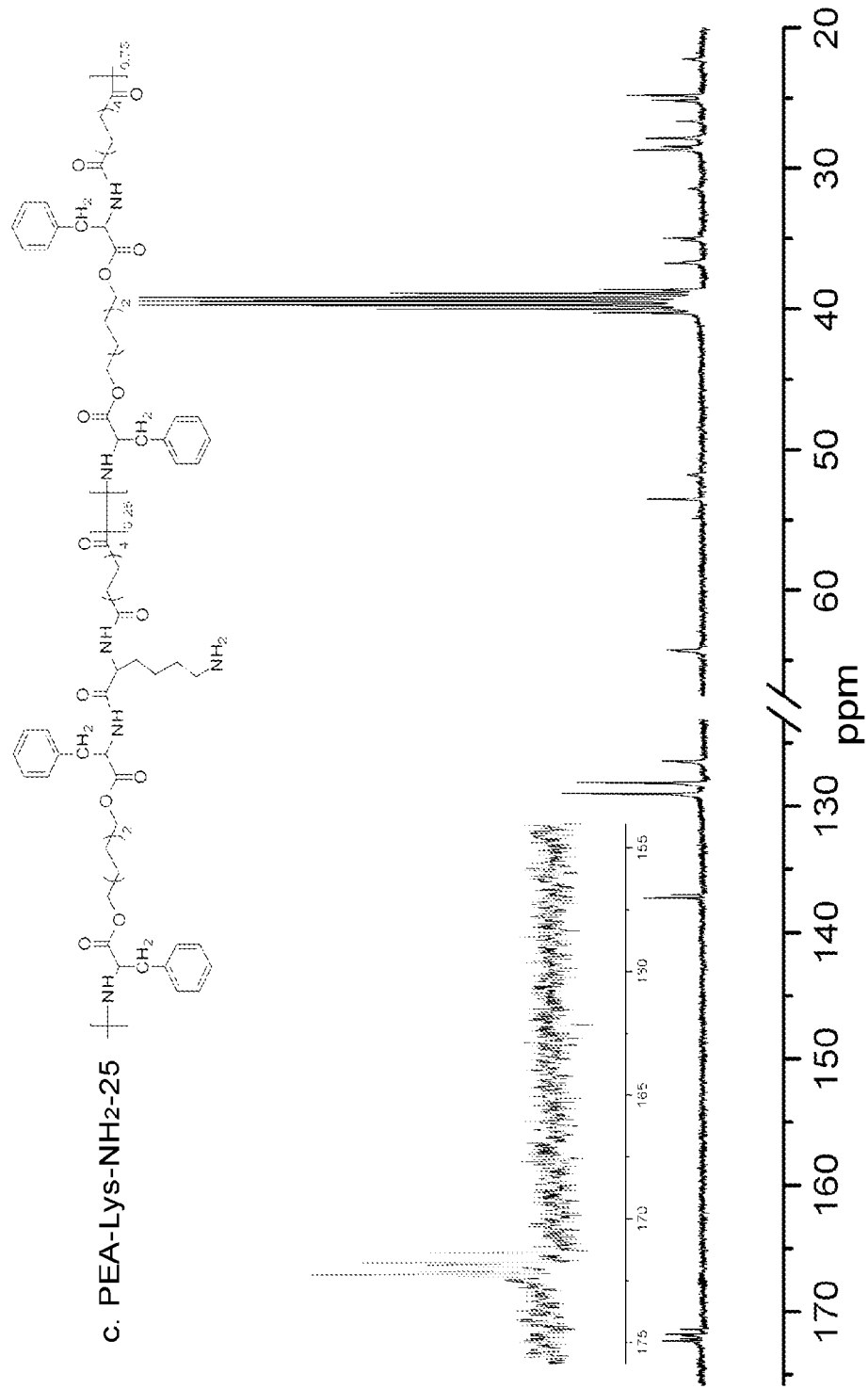

The benzyloxycaronyl (Z) protecting group on α-amino group of Lysine can be removed either by catalytic hydrogenolysis or catalytic transfer hydrogenation. However, the Z group on ω-amino position is usually removed under strong acid hydrolysis or catalytic hydrogenolysis. The removal of Z groups at the N-terminal Lysine units of PEA-Z-Lys was performed by treatment in the mixed solvent of methanesulfonic acid, anisole and trifluoroacetic acid for 1 hr and by subsequent neutralization with triethylamine. $^1$H NMR analysis of the PEA-Lys-NH$_2$ demonstrated almost complete removal of the protecting groups by the absence of proton peaks of Z group at 5.00 ppm (FIG. 4). In the $^{13}$C NMR spectrum, the disappearance of carbonyl carbon signal of Z group at 165 ppm confirmed the complete deprotection (FIG. 5).

Molecular weight loss of the deprotective PEAs during the removal of Z protecting groups was detected. As shown in Table 2, the molecular weight of PEAs (PEA-Z-Lys-05, PEA-Lys-NH$_2$-05) was reduced from 67,000 to 45,300 (32% molecular weight reduction) by the treatment with mix acid deprotection medium. The reduction in molecular weight of PEA-Lys-NH$_2$ became more pronounced as the Lys content increased. This molecular weight reduction upon the deprotection procedure could be attributed to (1) the loss of the Z protecting groups and (2) the partial hydrolysis of ester bonds in PEA backbone under the strong acid deprotection condition.

In order to directly demonstrate the existence of free amine groups, the NHS-fluorescein dye attached PEA has been synthesized as shown in Scheme 4.

Figure 6:
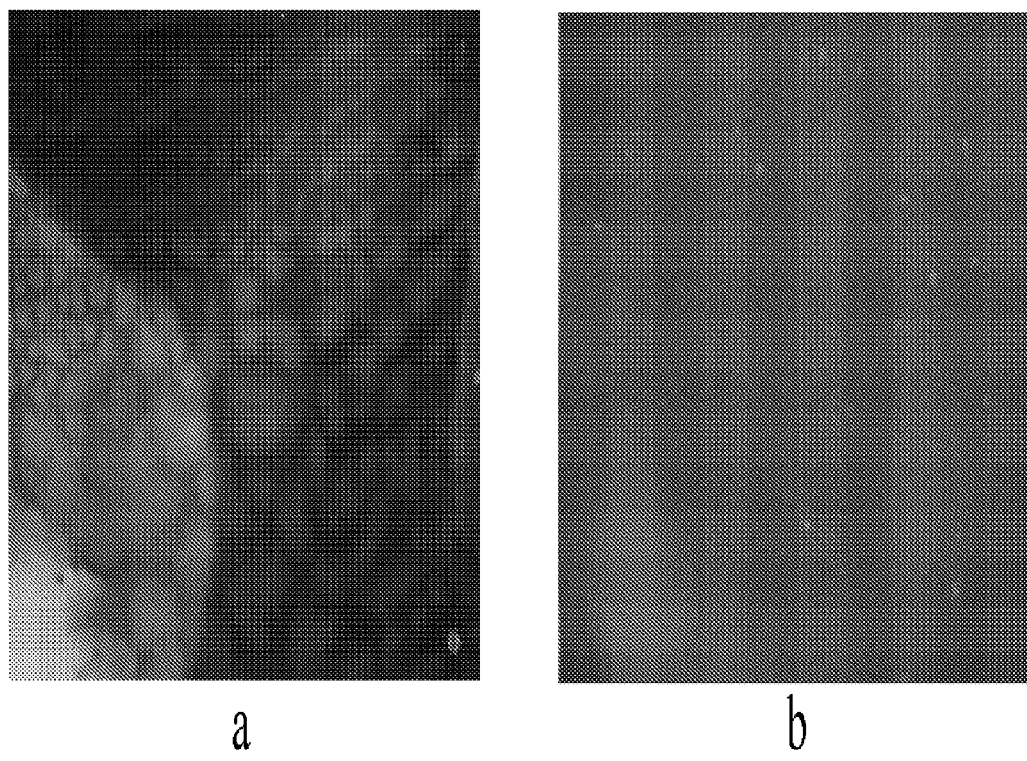
FIG. 6 shows a fluorescent microscope images PEA film on glass cover slips (a) PEA-Lys-05-Dye film on glass cover slip, and (b) PEA-Lys-NH$_2$-05.

This fluorescein dye is activated to react with amine groups and PEA. The left image in FIG. 6 shows that the NHS-fluorescein attached PEA sample displayed the characteristic green color. In contrast, the right image of control sample (PEA-Z-Lys-05) shows a distinct black color.

This family of PEA-Lys-NH$_2$ has two amino acids within the same repeating unit. Additionally, the PEA-Lys-NH$_2$ family provides functional free amine groups. In this regard the PEAs are negatively charged in a physiological pH.

Thermal Property

Figure 7:
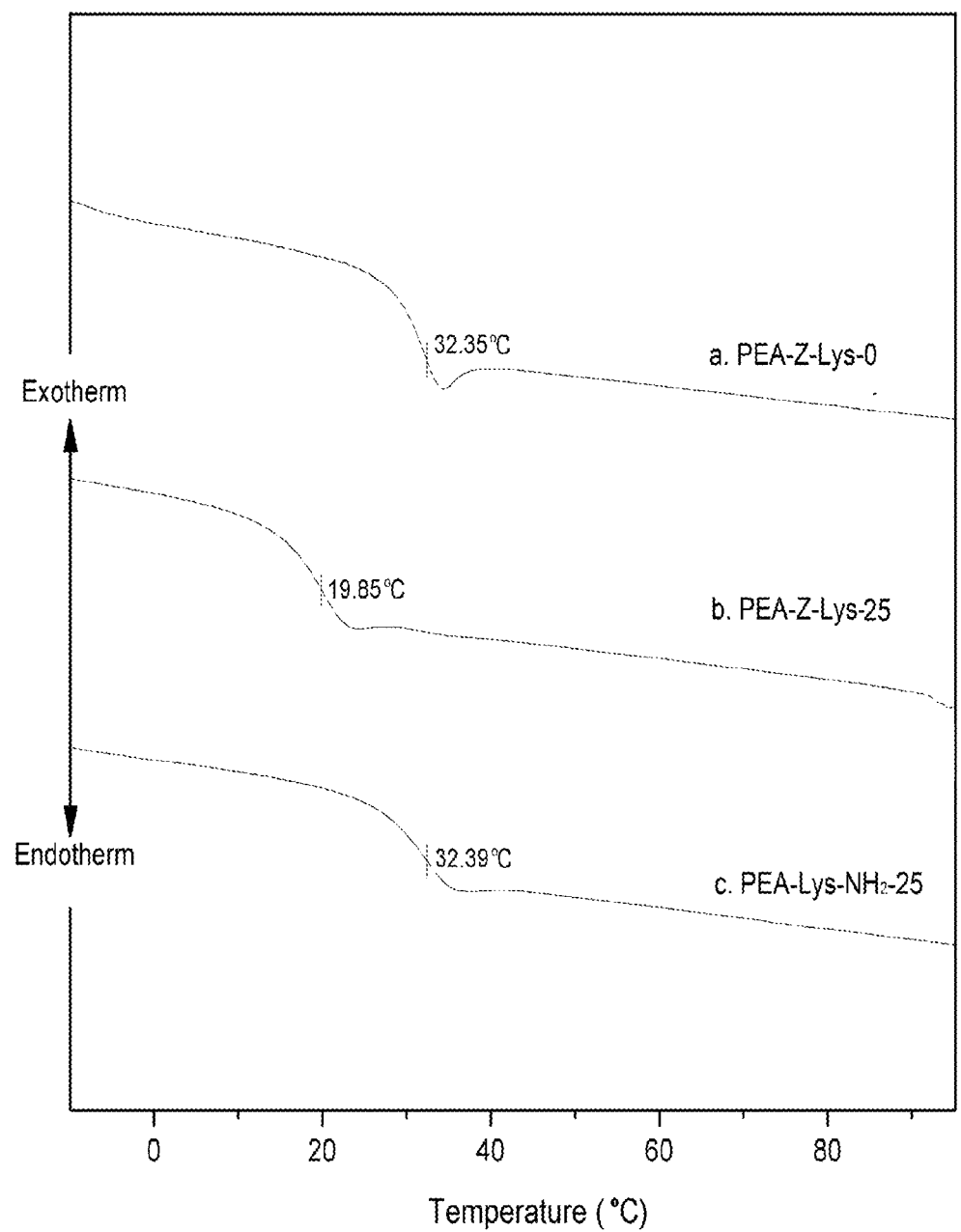
FIG. 7 illustrates the results of a DSC trace of three representative PEAs (a) PEA-Z-Lys-O, (b) PEA-Z-Lys-25, and (c) PEA-Lys-NH$_2$-25.

The glass transition temperatures ($T_g$) of the polymers listed in Table 2 were determined by differential scanning calorimetry (DSC). All PEA polymers having Lys content were amorphous and exhibited $T_g$ ranging from 18 to 32° C., no melting temperature was observed. Typical DSC traces of these PEAs are depicted in FIG. 7. For the PEA-Z-Lys-0 (PEA without Lys units), the $T_g$ is 32.35° C. The $T_g$ of PEA-Z-Lys-25 was 19.85° C., which shifts to a temperature of about 12° C. lower than that of PEA-Z-Lys-0. The reason of this reduction in $T_g$ is attributed to the presence of the flexible pendant protective group in the Lys unit, which acts as an internal plasticizer, lowering the frictional interaction between polymer chains. After deprotection, the recovered pendant amino group in the Lys unit strengthened the interaction between the polymeric chains via hydrogen bonds. Therefore, the deprotected PEA-Lys-NH$_2$-25 exhibited a higher $T_g$ ($T_g$=32.39° C.) than its protected PEA-Z-Lys-25 counterpart.

Figure 10:
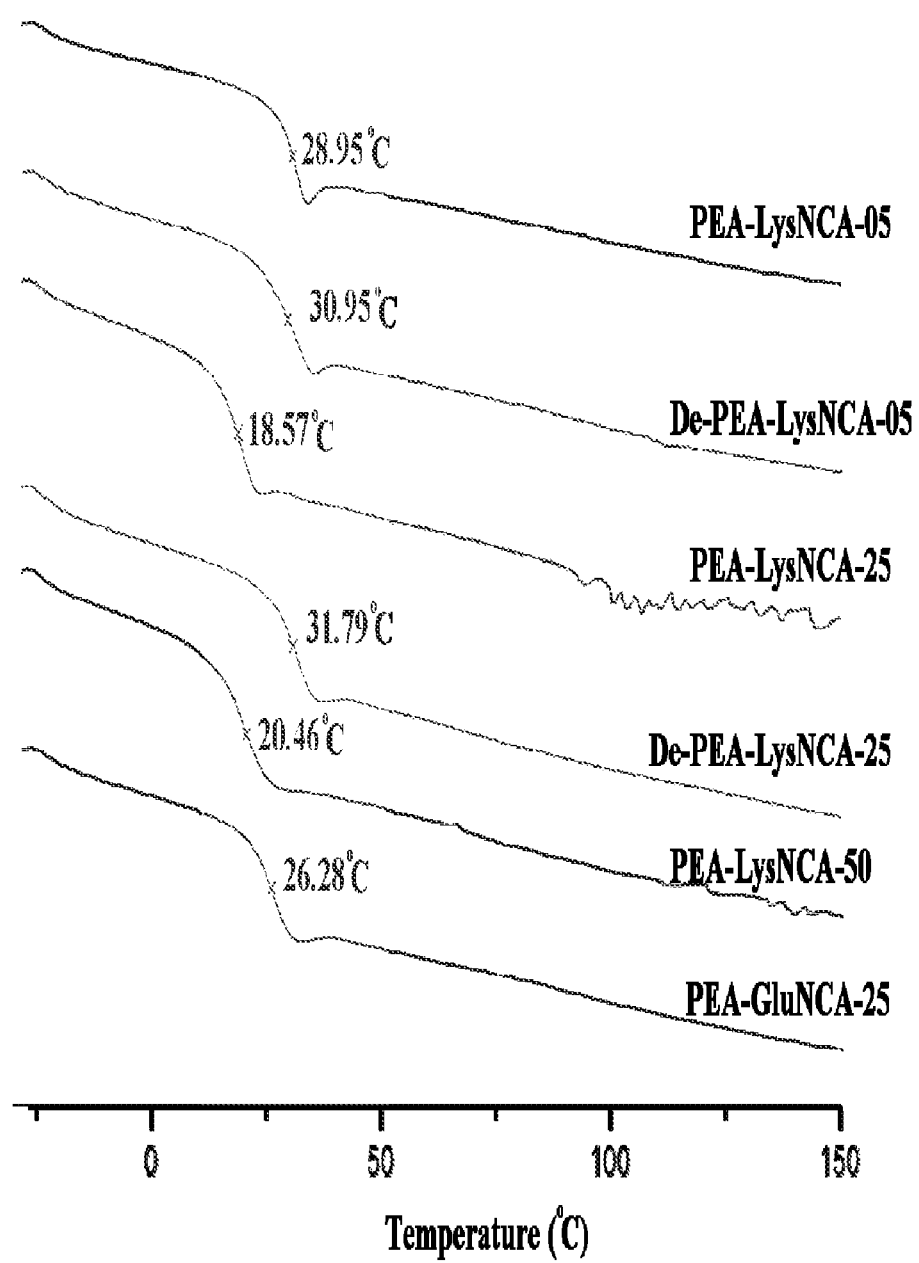
FIG. 10 shows that the presence of free amine groups on PEA reduce the flexibility of the polymer chains and increase the glass-transition temperature.

The chemical structure of PEA had an effect on $T_g$. The introduction of C=C double bond into the diols and dicarboxylic acid parts of PEA increases the rigidity of PEA polymer chain, and raises the $T_g$ up to 109° C. However, the strong intermolecular interaction of unsaturated PEAs is believed to result in their poor solubility in common organic solvents. The polymethylene chain length of PEA back-bone could also affect the flexibility of polymer chain and $T_g$. By changing the length of polymethylene chain on diols and dicarboxylic acid segments, the $T_g$ of resulting PEAs can be adjusted. The length of polymethylene chains at 6 and 8 on diols and dicarboxylic acid was found to provide a PEA with flexible properties and solubility. FIG. 10 shows that the presence of free amine groups on PEA reduce the flexibility of the polymer chains and increase the glass-transition temperature.

Solubility

Table 3 shows the solubility at room temperature of PEA-Z-Lys and PEA-Lys-NH$_2$ having different lysine contents. All the PEA-Z-Lys were completely soluble in polar solvents, such as CHCl$_3$, DMF and DMSO but could not dissolve in ethyl acetate, acetone and water. PEA-Lys-NH$_2$ are soluble in DMF and DMSO but not in water. The PEA-Lys-NH$_2$ having higher Lysine content, such as PEA-Lys-NH$_2$-50, forms strong hydrogen bonds and once dried, is difficult to re-dissolve.

TABLE 3

|  | H$_2$O | DMF | DMSO | THF | Methanol | Ethyl acetate | Chloroform | Acetone |
|---|---|---|---|---|---|---|---|---|
| PEA-Z-Lys-0 | − | + | + | + | − | − | + | − |
| PEA-Z-Lys-05 | − | + | + | + | − | − | + | − |
| PEA-Lys-NH$_2$-05 | − | + | + | ± | − | − | + | − |
| PEA-Z-Lys-15 | − | + | + | + | − | − | + | − |
| PEA-Lys-NH$_2$-15 | − | + | + | − | − | − | + | − |
| PEA-Z-Lys-25 | − | + | + | + | − | − | + | − |
| PEA-Lys-NH$_2$-25 | − | + | + | − | − | − | + | − |
| PEA-Z-Lys-35 | − | + | + | + | − | − | + | − |
| PEA-Lys-NH$_2$-35 | − | + | + | − | ± | − | ± | − |
| PEA-Z-Lys-50 | − | + | + | + | − | − | + | − |
| PEA-Lys-NH$_2$-50 | − | ± | ± | − | ± | − | − | − |

Figure 8:
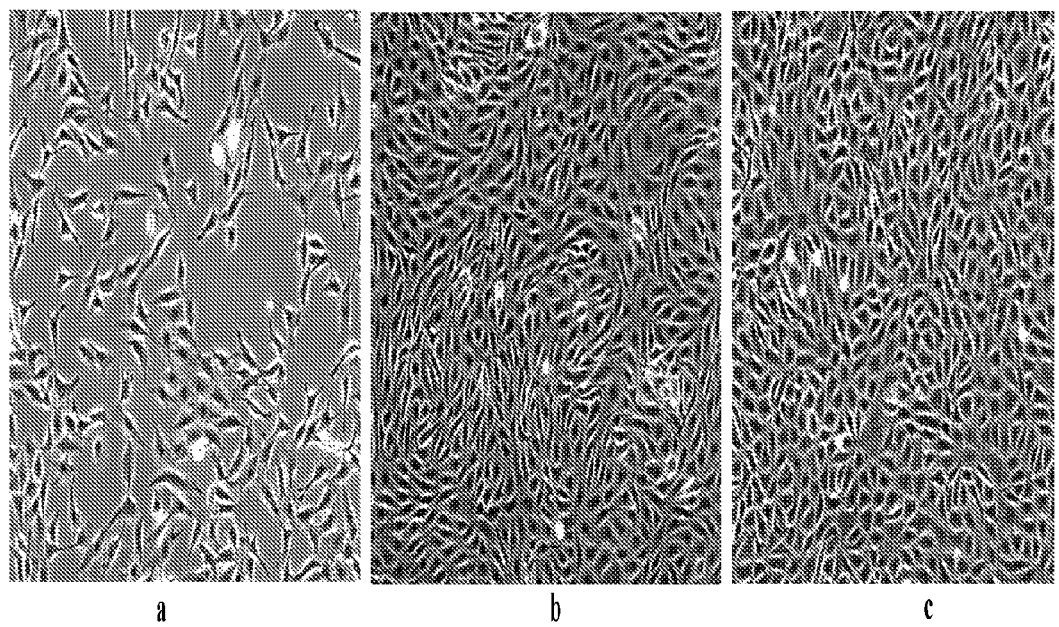
FIG. 8 shows microscopic images of adhered endothelial cells in the form of group: (a) Blank Control (without any treatment); (b) Gelatin Coated; and (c) PEA-Lys-NH$_2$-25 Coated.
Figure 9:
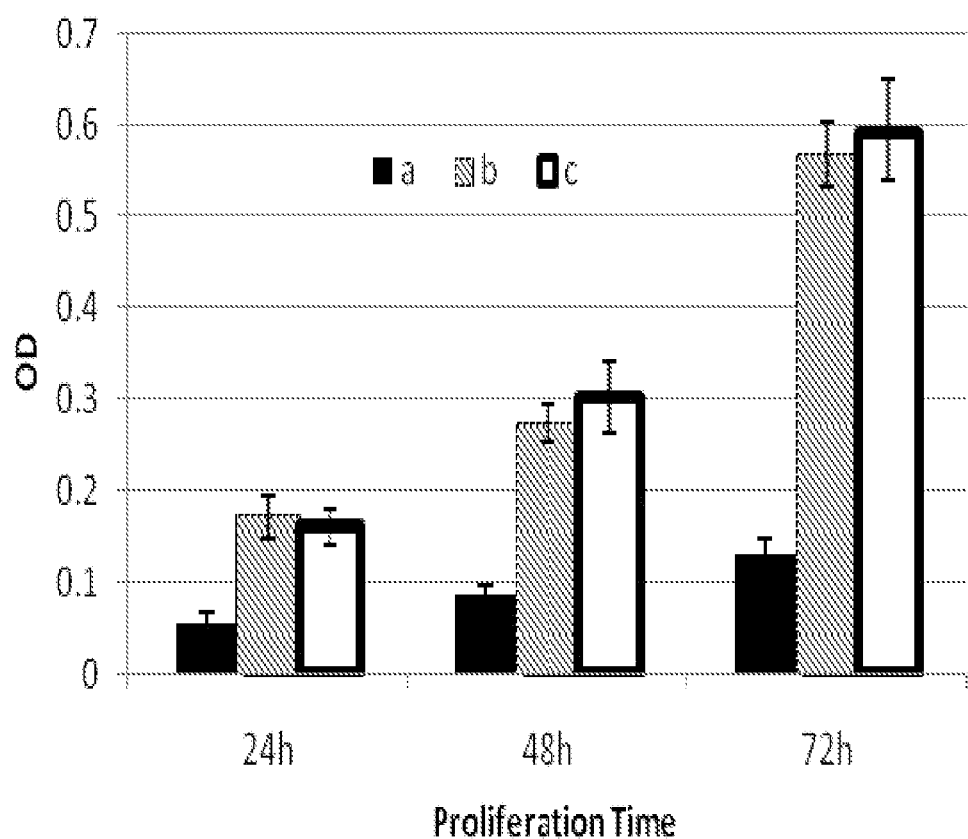
FIG. 9 shows the results of a proliferation assay of a (a) Blank Control (without any treatment); (b) Gelatin Coated; and (c) PEA-Lys-NH$_2$-25 Coated.

Solubility of PEA-Z-Lys and PEA-Lys-NH$_2$ at room Temperature (25° C.)$^a$
$^a$+ soluble; − insoluble; ± partially soluble or swelling Cell Adhesion and Proliferation The microscope images of FIG. 8 shows that both the gelatin-coated control and PEA-Lys-NH$_2$-25 coated groups show confluent BAEC (bovine aortic endothelial cells) cells after 3 days, while the untreated groups has less than 50% confluent. A MTT assay was used to test the living cells. FIG. 9 illustrates that the BAEC proliferation rate is slower in the blank group when compared with the coated-groups at all 3 periods. For the coated-groups, both of them showed high proliferation rates, and the PEA-Lys-NH$_2$-25 coated group showed same or slightly better cell proliferation.

EXAMPLE 2

Synthesis of PEA with Pendant COOH Groups

Synthesis of 8-Phe-4-Glu-COOH25

The reaction for 8-Phe-4-Glu-COOH25 is illustrated as follows:

Scheme 5

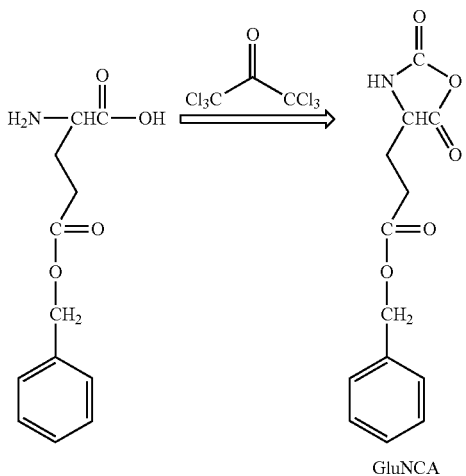

GluNCA

-continued
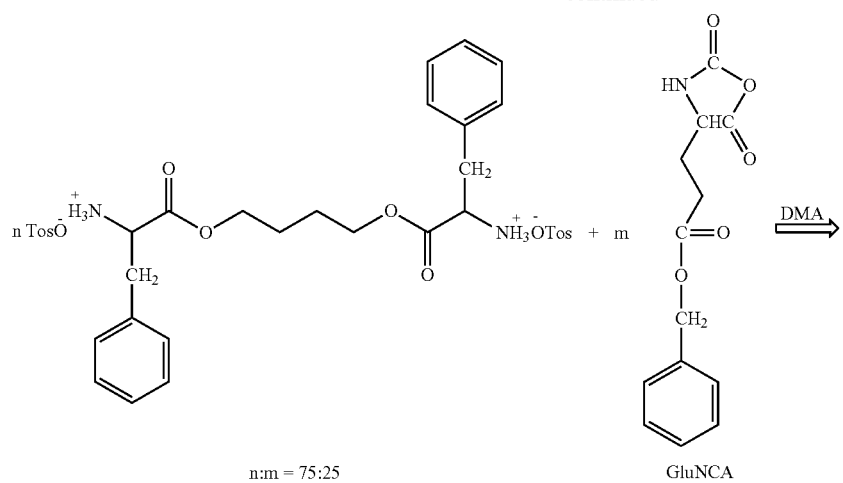
n:m = 75:25    GluNCA
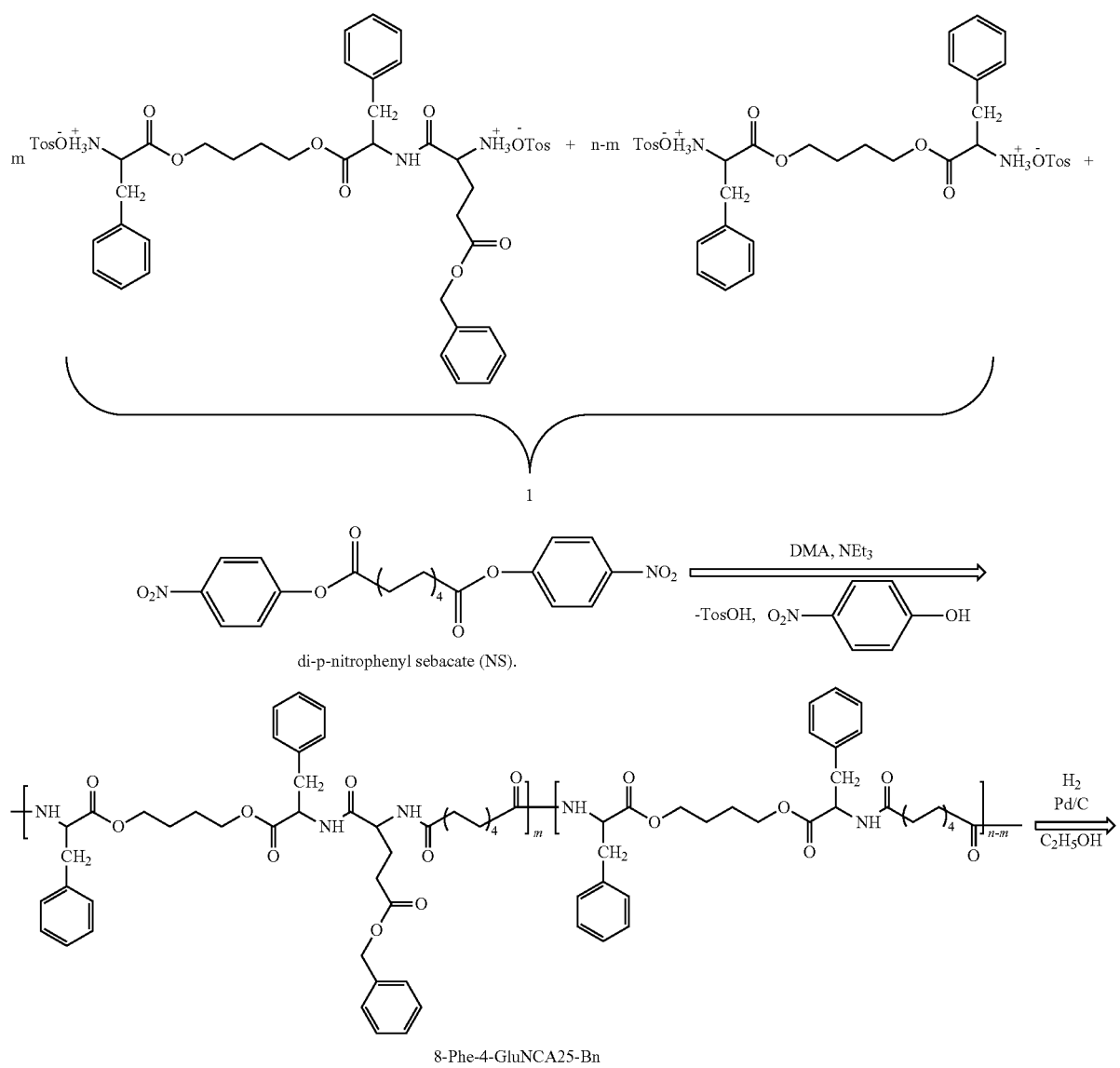
8-Phe-4-GluNCA25-Bn

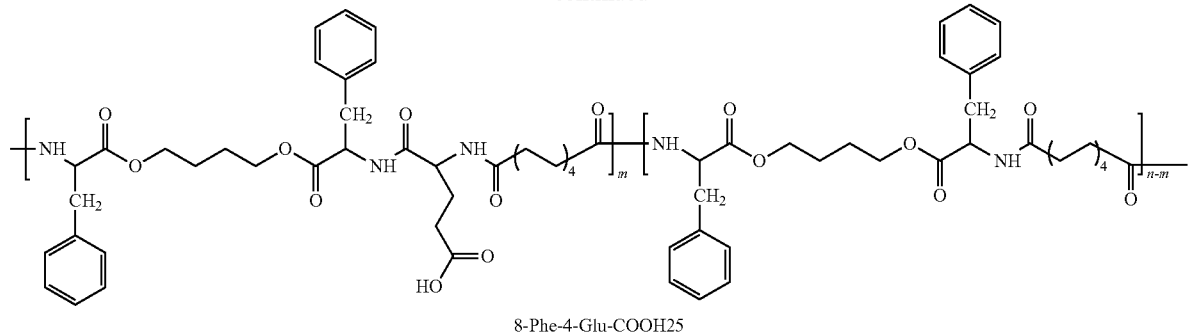

8-Phe-4-Glu-COOH25

Note: Bn = —CH₂—⌬

Synthesis of γ-benzyl-L-Glutamate N-carboxyanhydride (GluNCA)

A suspension of L-glutamic acid γ-genzyl ester (5.07 g, 21.40 mmol) in 150 mL of ethyl acetate was reflux in a nitrogen atmosphere. A solution of triphosgene (2.37 g, 8.00 mmol) dissolved in 30 mL ethyl acetate was added to the stirred reaction mixture. When the reaction mixture started to become transparent, a stream of nitrogen was bubbled through the solution to remove HCl. After the reaction was complete, the solvent was evaporated under vacuum to give a colorless oily residue which crystallized upon cooling in a refrigerator. For further purification the γ-benzyl-L-glutamate N-carboxyanhydride obtained, it was recrystallized three times in a mixture of ethyl acetate/petroleum ether and dried in vacuo. The yield was 79%.

A typical experimental procedure of the synthesis of derivative monomer 1 is given here. The molar ratio between Phe-4 and GluNCA was 75:25. GluNCA (1.00 g, 3.80 mmol) was added to a solution of Phe-4 (8.30 g, 11.40 mmol) in 30 mL of N,N-dimethylacetamide (DMA). The reaction mixture was stirred at 40° C. for 3 hrs and the solution temperature was raised to 80° C. for 24 hrs in a nitrogen atmosphere. The reaction was subsequently cooled to a room temperature and used in the next stage polycondensation reaction without further purification.

Synthesis of 8-Phe-4-Glu-25-Bn (Protected)

NS (5.06 g, 11.40 mmol) and dry NEt₃ (3.48 mL, 25.08 mmol) were added to a solution of derivative monomer 1 (8.04 g, 11.40 mmol) in 30 mL of DMA under nitrogen atmosphere. The reaction solution was stirred at room temperature for 5 min and subsequently at 80° C. for 24 hr. The resulting solution was cooled to room temperature, diluted with 30 ml of DMA and precipitated into an excess of cold ethyl acetate. Purification was performed by dissolving the polymer in dichloromethane and slowly adding into an excess of cold ethyl acetate. The tar-like polymer was isolated by filtration, and dried in vacuo at 50° C. Yield 75%.

Synthesis of 8-Phe-4-Glu-COOH25 (Deprotection Procedure)

8-Phe-4-Glu-25-Bn (3 g) was added to 50 mL ethanol in a 500 mL reaction flask. 10 wt % Pd/C (0.5 g, from Aldrich) was added into the flask under the protection of nitrogen. The reaction mixture was slowly heated to 70° C., and then the bubble gas was changed from nitrogen to hydrogen. The mixture was cooled to room temperature after 24 hrs catalytic hydrogenation reaction and the bubble gas was changed from hydrogen to nitrogen. The upper ethanol layer was dumped and the remaining polymer was dissolved the CH₂Cl₂. The Pd/C was removed by high-speed centrifugation. The purification procedure is the same as the preparation of 8-Phe-4-Glu-25-Bn.

EXAMPLE 3

Synthesis of PEA with Pendant OH Groups

Synthesis of 8-Val-4-Ser-OH25

The synthesis of 8-Val-4-Ser-OH25 is illustrated as follows:

Scheme 6

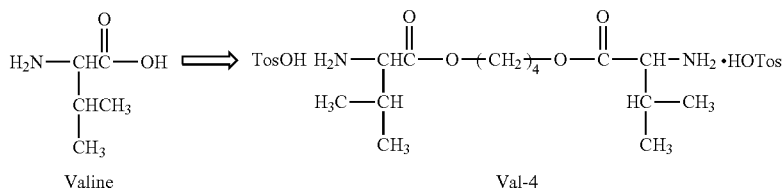

Valine          Val-4

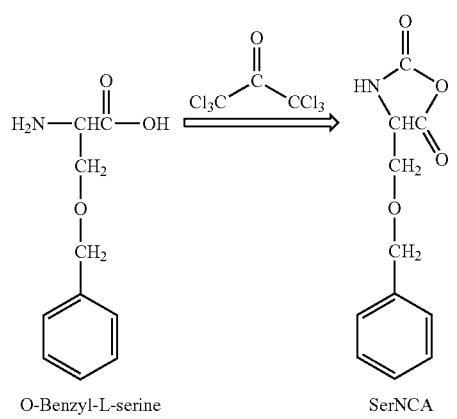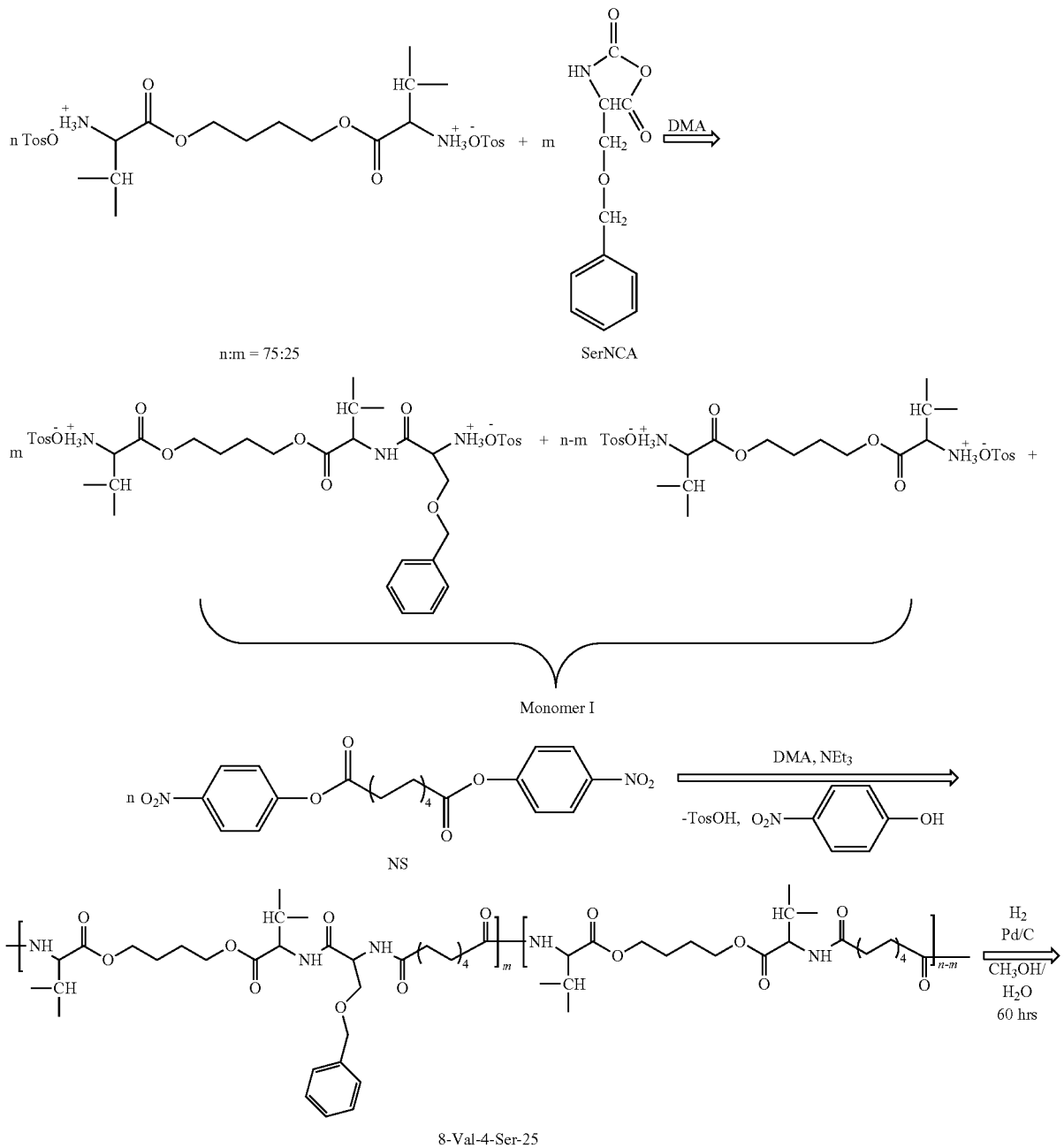

-continued

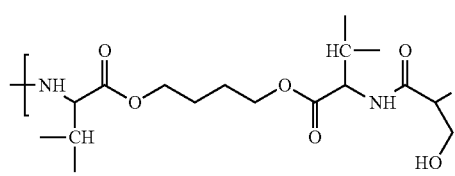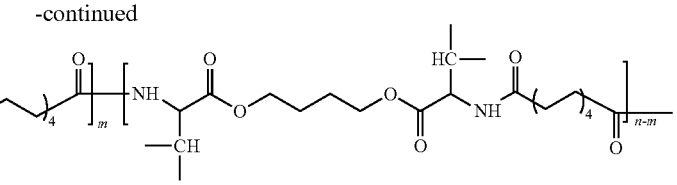

8-Val-4-Ser-OH25

Synthesis of Di-p-toluenesulfonic Acid Salts of Bis-L-valine butane-1,4-diester(Val-4)

The L-Valine (20.60 g, 0.176 mol), p-toluenesulfonic acid monohydrate (33.44 g, 0.176 mol) and 1,4-butanediol (7.2 g, 0.08 mol) in 300 mL of toluene were placed in a reaction flask with a Dean-Stark apparatus and stir bar. The solid-liquid reaction mixture was heated to reflux for 24 hrs and then cooled to room temperature. After the solvent was removed by evaporation, the crude product was purified by recrystallizing in water for 3 times, and try in vacuo.

Synthesis of O-benzyl-L-Serine N-carboxyanhydride (SerNCA)

A suspension of O-benzyl-L-Serine (4.18 g, 21.40 mmol) in 150 mL of ethyl acetate was reflux in a nitrogen atmosphere. A solution of triphosgene (2.37 g, 8.00 mmol) dissolved in 30 mL ethyl acetate was added to the stirred reaction mixture. When the reaction mixture started to become clear, a stream of nitrogen was bubbled through the solution to removed HCl. After the reaction was complete, the solvent was evaporated under vacuum to give a colorless oily residue which crystallized upon cooling in a refrigerator. For further purification the O-benzyl-L-Serine N-carboxyanhydride obtained, it was recrystallized three times in a mixture of ethyl acetate/petroleum ether and dried in vacuo.

Synthesis of Derivative Monomer 1 in Scheme 5 Synthesis of 8-Val-4-Ser-OH25

The molar ratio between Val-4 and SerNCA was 75:25. SerNCA (0.70 g, 3.18 mmol) was added to a solution of Val-4 (6.03 g, 9.54 mmol) in 30 mL of N,N-dimethylacetamide (DMA). The reaction mixture was stirred at 40° C. for 3 hrs and the solution temperature was raised to 80° C. for 24 hrs in a nitrogen atmosphere. The reaction was subsequently cooled to a room temperature and used in the next stage polycondensation reaction without further purification.

Synthesis of 8-Val-4-Ser-25

NS (4.24 g, 9.54 mmol) and dry NEt₃ (2.65 mL, 19.08 mmol) were added to a solution of derivative monomer 1 (9.54 mmol) in 30 mL of DMA under nitrogen atmosphere. The reaction solution was stirred at room temperature for 5 min and subsequently at 80° C. for 24 hr. The resulting solution was cooled to room temperature, diluted with 30 ml of DMA and precipitated into an excess of cold ethyl acetate. Purification was performed by dissolving the polymer in dichloromethane and slowly adding into an excess of cold ethyl acetate. The tar-like polymer was isolated by filtration, and dried in vacuo at 50° C.

Synthesis of 8-Val-4-Ser-OH25 (Deprotection Procedure)

8-Val-4-Ser25 (2 g) was added to 50 mL methanol and 2.5 mL distilled water mixture in a 500 mL reaction flask. 10 wt % Pd/C (0.5 g, from Aldrich) was added into the flask under the protection of nitrogen. The advantage of using methanol vs. ethanol is that the deprotection reaches near 100%, i.e., majority of the —OH group is recovered from the protected stage. The reaction mixture was slowly heated to 70° C., and then the bubble gas was changed from nitrogen to hydrogen. The mixture was cooled to room temperature after 60 hrs catalytic hydrogenation reaction and the bubble gas was changed from hydrogen to nitrogen. The upper ethanol layer was dumped and the remaining polymer was dissolved the $CH_2Cl_2$. The Pd/C was removed by high-speed centrifugation. The purification procedure is the same for 8-Val-4-Ser25.

Synthesis of Acrylate Derivative of 8-Val-4-Ser-OH25

As shown in the Scheme 5, 8-Val-4-Ser-OH25 (1 g) was dissolved in anhydrous tetrahydrofuran (20 mL), and the solution was added into a three-necked flask which equipped with magnetic stirrer and a dropping funnel. The contents of the flask was cooled to 0° C., and triethylamine (0.15 g, 1.48 mmol) was added. The solution was stirred, and then, freshly distilled acryloyl chloride (0.13 g, 1.48 mmol) in 10 mL THF was drop wisely added to the solution. The stirring was continued for 2 hrs at 0° C. then for 12 hrs at room temperature. The purification procedure is the same for 8-Val-4-Ser25.

EXAMPLE 4

Photo-UV Gelation of the Acrylate Derivative of 8-Val-4-Ser-OH25

A 20% w/v solution of 0.12 g of acrylate derivative of 8-Val-4-Ser-OH25 and Irgacure 2959 photo-initiator (5% w/w on the basis of acrylate derivative of 8-Val-4-Ser-OH25) dissolved in DMSO was prepared. The solution was added into Teflon mold and irradiated by a 100 W medium-pressure mercury ultraviolet lamp for 20 min. A gel was produced. The reaction is illustrated as follows:

Scheme 7

8-Val-4-Ser-OH25

Acrylate Derivative of 8-Val-4-Ser-OH25

Cross-linked network (Gel)

EXAMPLE 5

A free amine groups on a de protected PEA-LysNCA-25 compound is used to make a gel via glutaraldehyde. 0.15 g deprotected PEA-LysNCA-25 was dissolved in 5 mL DMF at room temperature. 4 drops of Glutaraldehyde (50% in water) was added under stirring in a vial. The solution turned into gel after a few minutes.

EXAMPLE 6

0.15 g PEA-COOH-25 and 0.15 g De-PEA-LysNCA-25 were dissolved in 5 mL DMF at room temperature, a molar equivalent of carbonyldiimidazole was added under stirring. After 12 hours, the solution becomes a transparent gel.

EXAMPLE 7

PEA-AspNCA-25 can be produced in a manner consistent with EXAMPLE 3. A gel is produced by dissolving 0.25 g of chitosan and 0.15 g deprotected PEA-AspNCA-25 in 5 mL DMF at room temperature, adding a molar equivalent of carbonyldiimidazole under stirring to form a transparent gel.

EXAMPLE 8

PEA-GluNCA-25 can be produced in a manner consistent with EXAMPLE 2. A gel is produced by dissolving 0.25 g of chitosan and 0.15 g deprotected PEA-GluNCA-25 in 5 mL DMF at room temperature, and adding a molar equivalent of carbonyldiimidazole under stirring to form a transparent gel.

What is claimed:

1. A poly(ester amide) (PEA) of formula (I):

wherein m is 0.1 to 0.9;
n is 0.9 to 0.1,
wherein n is greater than or equal to m;
$R^3$ is a residue of a first amino acid having a substituent group that does not need protection during peptide synthesis;
$R^4$ and $R^6$ are ($C_2$-$C_{20}$) alkylene; and
$R^5$ is a residue of a second amino acid which has a pendant group selected from the group consisting of $NH_2$, COOH, and OH, and
wherein the second amino acid is the same or different as the first amino acid, and
wherein the pendant group is optionally protected, and
wherein the PEA has a Mn of 1 to 500 kg/mol.

2. The PEA according to claim 1, wherein $R^3$ is selected from the group consisting of $CH_2$—C$_6$H$_5$, $(CH_2)_3$—NH—C(NH)—$NH_2$, $CH(CH_3)_2$, $CH_2CH(CH_3)_2$, $CH(CH_3)CH_2CH_3$, $(CH_2)CH_3$, H, $CH_3$, and $(CH_2)_2SCH_3$;
$R^5$ is selected from the group consisting of $(CH_2)_4NH_2$, $CH_2OH$, $CH_2COOH$, and $(CH2)_2COOH$.

3. The PEA according to claim 2, wherein $R^3$ is $CH_2$—C$_6$H$_5$ or $(CH_2)_3$—NH—C(NH)—$NH_2$, and $R^5$ is $(CH_2)_4NH_2$.

4. The PEA according to claim 1, wherein $R^5$ is selected from the group consisting of $(CH_2)_4NH_2$, $CH_2OH$, $CH_2COOH$, and $(CH_2)_2COOH$.

5. The PEA according to claim 1, wherein the pendant group of said residue of a second amino acid is modified with a protective group.

6. A composition comprising the PEA according to claim 1.

7. A polymer of formula (X):

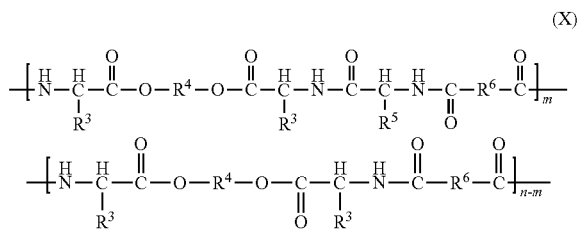

wherein m is 0.1 to 0.9;
n is 0.9 to 0.1,
wherein n is greater than or equal to m;
$R^3$ is a residue of a first amino acid having a substituent group that does not need protection during peptide synthesis;
$R^4$ and $R^6$ are selected from the group consisting of ($C_2$-$C_{28}$) alkyloxy; ($C_2$-$C_{28}$) alkylene; ($C_2$-$C_{28}$) alkyloxy substituted with a side chain selected from the group consisting of (2-carboxyethyl)thio, (2-hydroxethyl)thio, (2-aminoethyl)thio and (2-aminoethyl)thio hydrochloride salt; or ($C_2$-$C_{28}$) alkylene substituted with a side chain selected from the group consisting of (2-carboxyethyl)thio, (2-hydroxethyl)thio, (2-aminoethyl)thio, and (2-aminoethyl)thio hydrochloride salt; and $R^5$ is a residue of a second amino acid has a pendant group selected from the group consisting of $NH_2$, $COOH$, and $OH$, and wherein the second amino acid is the same or different as the first amino acid, and wherein the pendant group is optionally protected, and wherein the polymer has a Mn of 1 to 500 kg/mol.

8. The polymer according to claim 7, wherein $R^3$ is selected from the group consisting of

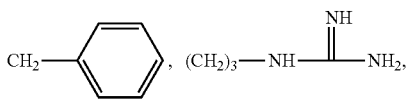

$CH(CH_3)_2$, $CH_2CH(CH_3)_2$, $CH(CH_3)CH_2CH_3$, $(CH_2)CH_3$, H, $CH_3$, and $(CH_2)_2SCH_3$;

$R^5$ is selected from the group consisting of $(CH_2)_4NH_2$, $CH_2OH$, $CH_2COOH$, and $(CH_2)_2COOH$.

9. The polymer according to claim 8, wherein $R^3$ is

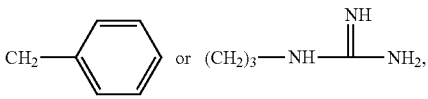

and $R^5$ is $(CH_2)_4NH_2$.

10. The polymer according to claim 8, wherein the pendant group of said residue of a second amino acid is modified with a protective group.

11. The polymer according to claim 7, wherein $R^5$ is selected from the group consisting of $(CH_2)_4NH_2$, $CH_2OH$, $CH_2COOH$, and $(CH_2)_2COOH$.

* * * * *